(12) United States Patent
Duensing et al.

(10) Patent No.: US 10,539,635 B2
(45) Date of Patent: Jan. 21, 2020

(54) ADJUSTABLE RF COIL ASSEMBLY FOR MAGNETIC RESONANCE SYSTEMS AND METHOD OF OPERATION THEREOF

(71) Applicant: KONINKLIJKE PHILIPS N.V., Eindhoven (NL)

(72) Inventors: George Randall Duensing, Gainsville, FL (US); Ron Kosal, Gainsville, FL (US); Tracy Wynn, Gainsville, FL (US); Olli Tapio Friman, Gainsville, FL (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/767,837

(22) PCT Filed: Oct. 11, 2016

(86) PCT No.: PCT/EP2016/074309
§ 371 (c)(1),
(2) Date: Apr. 12, 2018

(87) PCT Pub. No.: WO2017/067815
PCT Pub. Date: Apr. 27, 2017

(65) Prior Publication Data
US 2018/0306877 A1 Oct. 25, 2018

Related U.S. Application Data

(60) Provisional application No. 62/243,327, filed on Oct. 19, 2015.

(51) Int. Cl.
*G01V 3/00* (2006.01)
*G01R 33/34* (2006.01)
*G01R 33/3415* (2006.01)
*A61B 5/055* (2006.01)

(52) U.S. Cl.
CPC ... *G01R 33/34007* (2013.01); *G01R 33/3415* (2013.01); *G01R 33/34084* (2013.01); *A61B 5/055* (2013.01)

(58) Field of Classification Search
CPC .................................. G01R 33/34007
USPC ............................. 324/318, 322
See application file for complete search history.

(56) References Cited

U.S. PATENT DOCUMENTS

| 5,343,862 A | 9/1994 | Jones |
| 6,577,888 B1* | 6/2003 | Chan .................... A61B 5/0555 324/318 |
| 6,778,849 B1 | 8/2004 | Ninomiya et al. |
| 7,049,819 B2 | 5/2006 | Chan et al. |

(Continued)

*Primary Examiner* — Louis M Arana

(57) ABSTRACT

A radio-frequency (RF) coil apparatus for magnetic resonance (MR) systems (100, 200, 300, 400, 500, 600, 700, 900, 1000) includes a base (102, 502, 702, 902, 1002) having opposed sides (121), a surface (124) to support an object of interest (OOI) for scanning, and fasteners (127) situated at the opposed sides, A positioner (104, 304A, 304B, 504, 604, 704, 1004) is configured to be releasably attached to the base and has a body (130) extending between opposed ends and fasteners (134,) situated at the opposed ends of the body, The body is configured to form an arch between the opposed ends. An upper section (106, 606, 706, 906, 1006) has at least one RF coil array (142) for acquiring induced MR signals, and is configured to be positioned over the positioner.

20 Claims, 17 Drawing Sheets

(56) References Cited

U.S. PATENT DOCUMENTS

| | | |
|---|---|---|
| 7,288,938 B2 | 10/2007 | Chmielewski et al. |
| 7,394,256 B2 | 7/2008 | Schubert et al. |
| 7,526,330 B1 | 4/2009 | Randell et al. |
| 7,659,719 B2 | 2/2010 | Vaughan et al. |
| 7,906,966 B1 | 3/2011 | Votruba |
| 9,615,770 B2 * | 4/2017 | Rohr .................... A61B 5/0555 |
| 2012/0256633 A1 | 10/2012 | Biber et al. |
| 2018/0136293 A1 * | 5/2018 | Xie ........................ A61B 5/055 |

* cited by examiner

ADJUSTABLE RF COIL ASSEMBLY FOR MAGNETIC RESONANCE SYSTEMS AND METHOD OF OPERATION THEREOF

CROSS REFERENCE TO RELATED APPLICATIONS

This application is a U.S. national phase application of International Application No. PCT/EP2016/074309, filed on Oct. 11, 2016, which claims the benefit of U.S. provisional Application Ser. No. 62/243,327 filed on Oct. 19, 2015 and is incorporated herein by reference.

The present system relates to adjustable radio frequency (RF) coils for magnetic resonance (MR) imaging (MRI) and spectroscopy (MRS) systems and, more particularly, to anatomically-shaped adjustable RF coils for MRI and MRS systems, and methods of operation thereof.

Typically, an RF coil for imaging parts is embedded in a body (e.g., fixed-array coil) of an MRI and is sized to fit a largest object of interest (OOI) that is intended for imaging. These coils are typically rigid and must be shaped and sized so that they are large enough to accommodate the largest envisioned OOI (e.g., the largest patient). This may result in a fixed-array coil having a large minimum volume. However, when a fixed-array coil with a large minimum volume is used to scan a smaller OOI (e.g., a small patient), it may not fit snugly against the OOI due to its volume. This may result in poor image performance, as it is well established that the best imaging performance may be possible when an RF coil fits snugly around an OOI and has the smallest imaging volume that can accommodate the OOI being scanned.

To solve the problem of bad imaging when a small OOI is imaged, RF coils that can be positioned closer to the OOI were developed. For example, for imaging parts of a body, such as knees, elbows, and the like, one solution is to use RF receive coils that are separate from the body of the MRI. However, these prior systems have significant problems including ease of use and the ability to produce satisfactory images. For example, one prior system for imaging a knee requires the individual coil portions to be fixedly fastened together prior to being positioned around the knee to create a fixed size volume that may be imaged. With this system, where the sizing is not suitable, the coil must be removed and resized to adjust the imaging volume. In another prior system, a coil consisting of a lower part rigidly locked onto a baseplate is provided. In operation, the patient is then placed into position on the lower part and the upper part is placed over the patient and locked onto the lower part in a single fixed position. This solution is hard to utilize since it has been found that it is desirable that the top part of the coil is adjustable to varying heights to accommodate a greater range of patient sizes. Also, in this system during the positioning and locking of the upper part to the lower part, the patient anatomy is not visible and there are risks in squeezing or pinching the patient anatomy between the coil parts or simply not properly positioning the coil in relation to the OOI. Similarly it is desirable that the coil is close to the patient's anatomy for scanning the OOI including a portion of the patient's anatomy. Unfortunately, these prior coils may experience large variations in performance for example due to variations in tuning that result from distortions of receive loops, variations in proximity between these loops, and/or the distance between the loops and the patient's anatomy. Another problem with these coils are mechanical locking features that make the coils more expensive and prone to mechanical failure. In addition, these coils often lack real positioning assist to indicate a preferred coil positioning with relation to the patients anatomy and specific coil positioning features.

Accordingly, embodiments of the present system may overcome these and other disadvantages of conventional MRI and MRS systems.

The system(s), device(s), method(s), arrangements(s), user interface(s), computer program(s), processes, etc. (hereinafter each of which will be referred to as a system, unless the context indicates otherwise), described herein may address one or more problems in the prior art systems.

In accordance with embodiments of the present system, there is disclosed a radio-frequency (RF) coil apparatus for magnetic resonance (MR) systems, the RF coil includes: a base having opposed sides, a surface to support an object of interest (OOI) for scanning, and fasteners situated at the opposed sides; a positioner configured to be releasably attached to the base and having a body extending between opposed ends and fasteners situated at the opposed ends of the body, the body configured to form an arch between the opposed ends; and an upper section having at least one RF coil array for acquiring induced MR signals, the upper section configured to be positioned over the positioner. The fasteners of the positioner may be configured to couple to corresponding fasteners of the base. The fasteners of the base and the positioner may be corresponding hook-and-loop type fasteners.

In accordance with embodiments of the present system, at least one of the fasteners of the positioner may comprise a tab suitable for grasping by a user. The positioner may be formed from a sheet of transparent, semi-transparent, or translucent plastic. The positioner may further comprise opposed flanges situated between the opposed ends. The opposed flanges may be configured to align the upper section in a desired position relative to at least one of the positioner and the base. The positioner may be further configured to support the upper section at a desired height. At least a portion of the positioner may be situated between the base and the upper section. The positioner may include at least one landmark for alignment relative to the OOI. The base may further comprise at least one RF coil array for acquiring induced MR signals. A communication link may be configured to couple the base and the upper section.

In accordance with embodiments of the present system, there is disclosed a radio-frequency (RF) coil apparatus for magnetic resonance (MR) systems, the RF coil includes: a base having opposed sides, a surface configured to support an object of interest (OOI) for scanning, fasteners situated at the opposed sides and at least one RF coil array configured to acquire induced MR signals; a positioner having a body including fasteners situated at a periphery of the body, the body being shaped to form at least a portion of an arch, and the fasteners being configured to be releasably attached to adjacent fasteners of the base; and an upper section having at least one RF coil array for acquiring induced MR signals and being configured to slide over at least a portion of the positioner. The positioner may further comprise opposed flanges. The opposed flanges may position the upper section relative to at least one of the positioner and the base.

In accordance with embodiments of the present system, there is disclosed a process of configuring a radio-frequency (RF) coil for scanning an object of interest (OOI), the process includes: acts of positioning the OOI upon a support surface of a base, the base having opposed sides and fasteners situated on each of the opposed sides; aligning a positioner with the OOI, the positioner having an arched body extending between opposed ends and fasteners situated at the opposed ends of the body; coupling the positioner to the base by attaching the fasteners of the positioner to adjacent corresponding fasteners of the base; and guiding, by the positioner, an upper section into a desired position relative to the OOI, the upper section having at least one RF coil array for acquiring induced MR signals, the upper section configured to slide over the positioner. The method may further include one or more acts of coupling a communication link between the base and the upper section, supporting the upper section by the positioner, and enhancing rigidity of the positioner using the upper section.

The present invention is explained in further detail in the following exemplary embodiments and with reference to the figures, where identical or similar elements are partly indicated by the same or similar reference numerals, and the features of various exemplary embodiments being combinable. In the drawings.

The following are descriptions of illustrative embodiments that when taken in conjunction with the following drawings will demonstrate various aspects of the claimed invention. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

For the sake of clarity, embodiments of the present system will be shown and described with respect to knee-type RF coils (e.g., knee coils). However, it is also envisioned that embodiments of the present system may include other shapes and/or sizes so that they are compatible with other desired parts of a body such as shoulders, wrists, elbows, necks, etc., without significant modifications.

Figure 1:
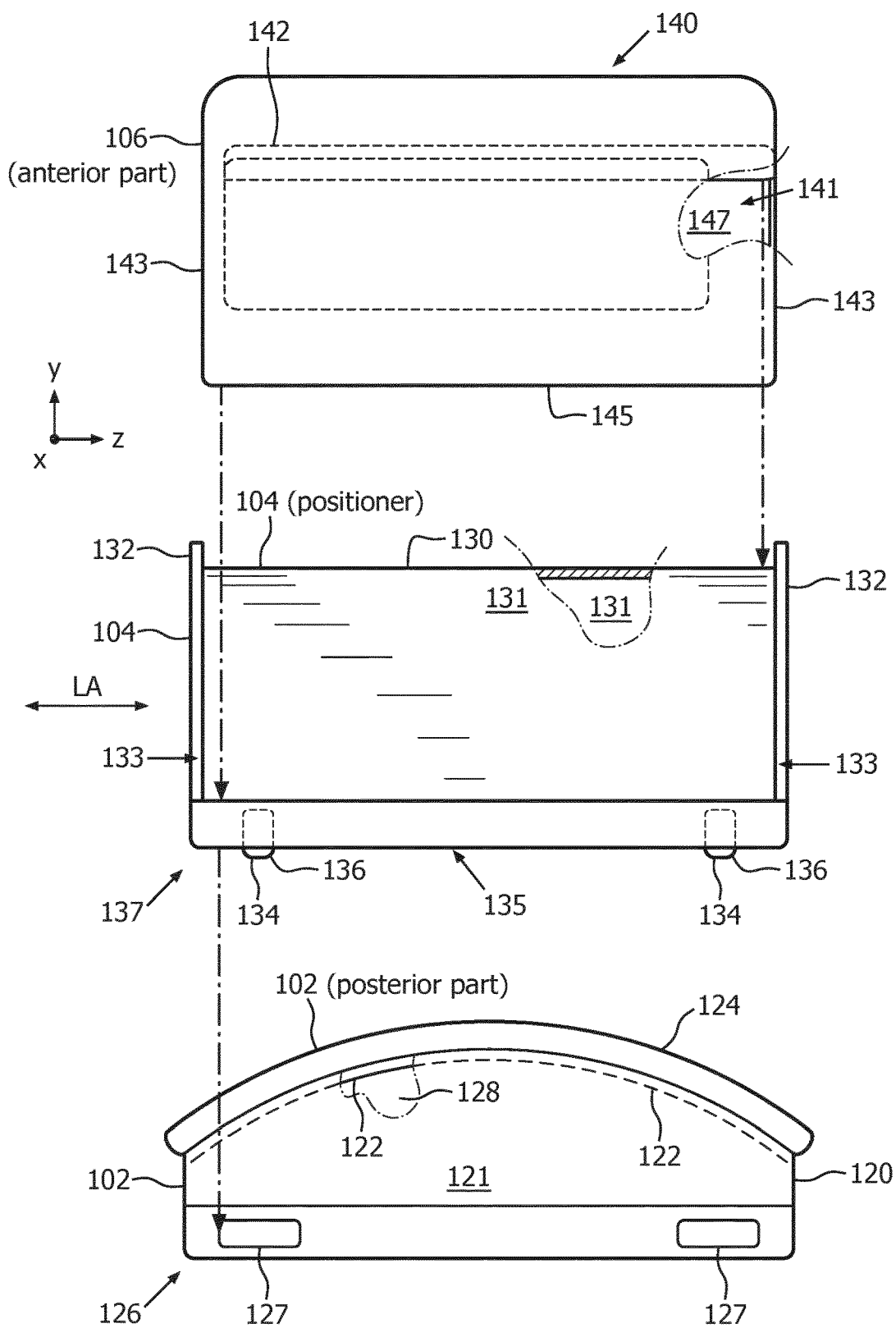
FIG. 1 shows a partially cutaway exploded front side view of a portion of an RF coil system operating in accordance with embodiments of the present system.

FIG. 1 shows a partially cutaway exploded front side view of a portion of an RF coil system 100 (hereinafter system 100 for the sake of clarity) operating in accordance with embodiments of the present system. The system 100 may include one or more of a base 102 (e.g., a posterior coil part or posterior housing), a positioner 104, and an upper section 106 (e.g., an anterior coil part or anterior housing). At least one of the base 102, the positioner 104 and the upper section 106 may include one or more RF coil arrays which may at least receive induced MR signals. The received induced MR signals may then be provided to a controller of the system 100 which may be part of the base 102 and/or upper section 106. It is also envisioned that the RF coil array(s) may include transmit and/or receive type RF coil arrays.

The base 102 may include one or more of a body 120, an RF coil array 122, a support 124, and an attachment mechanism 126. The attachment mechanism 126 may include any suitable fastener or fasteners to releasably fasten the positioner 104 to the base 102 in a desired position. For example, the attachment mechanism 126 may include a hook-and-loop type fasteners (e.g., Velcro™, etc.) such as fasteners 127 situated on opposed sides 121 (only one side is shown) of the body 120. Although discrete fasteners 127 are shown, it is also envisioned that the fasteners may include a continuous or substantially continuous strip which may extend across each side and/or from side to side of the opposed sides 121. For example, it is also envisioned that in embodiments of the present system, the fasteners may 127 may continuously or substantially continuously extend about the body 120. Further, it is envisioned that a single hook-and-loop type fastener may extend about the opposed sides 121 of the body 120. Further, although the hook-and-loop fasteners are illustrated as strips, it is envisioned that they may assume other shapes such as square, round, rectangular, etc. The fasteners 127 may be attached to the body 120 using any suitable method such as adhesives, mechanical fastening, etc., that are suitable for the material utilized in forming the body 120.

The body 120 may define one or more cavities such as at least one cavity 128 in which the RF coil array 122 and/or a controller (e.g., one or more processors) may be situated. In accordance with further embodiments of the present system, the RF coil array 122 and/or a controller (e.g., one or more processors) may be formed within the body 120.

In accordance with further embodiments of the present system, the support 124 may be anatomically shaped to support a desired OOI. For example, the support 124 may include an arc as shown to support a knee when the system 100 is configured to function as a knee coil. The support 124 may be padded to enhance patient comfort, as desired. However, it is also envisioned that yet other embodiments of the present system may include a support having other shapes and/or sizes to anatomically support other desired OOIs such as shoulders, elbows, necks, ankles, etc. as may be desired with minimal modification.

In accordance with embodiments of the present system, the positioner 104 may include one or more of a body 130 and an RF coil array. The positioner 104 may have opposed major surfaces 131, opposed edges 133, and opposed ends 135. The body 130 may be formed from a thin shell formed from one or more materials such as a plastic, methyl methacrylate, vinyl, poly-vinyl, and/or other material(s) that may be suitably formed and applied.

In accordance with embodiments of the present system, the positioner 104 may be formed as a translucent and/or semi-translucent shell. In these embodiments, the OOI is visible or partially visible through the positioner 104 which assists in proper positioning of the positioner 104 to assist in maximizing an imaging response received by the knee coil. The positioner 104 may include landmarks such as graphics which a user such as a clinician may use to properly align the positioner 104 with regard to the OOI and/or other portions of the system. Further discussion of the landmarks is made with regard to FIG. 3A which are intended to be optionally applicable in accordance with each of the embodiments shown in the figures.

In accordance with embodiments of the present system, the translucent plastic shell may be gradually folded or otherwise bent depending on the OOI, for example with regard to a knee, so as to form a "C" or "U" shape when attached to the base 102 as illustratively described and shown herein. In accordance with embodiments of the present system, the positioner 104 may be formed of a ridged and/or semi-ridged (e.g., part formed from ridged material, such as translucent plastic, and part form flexible material, such as a flexible sheet of methyl methacrylate). In an embodiment wherein the positioner 104 is formed of ridged material, the ridged shape is formed to complement the shape of the OOI (e.g., knee) and to complement the shape of the upper section 106 (e.g., see, FIG. 2A).

In accordance with further embodiments of the present system, the positioner 104 may include an attachment mechanism 137 which may complementary couple to the attachment mechanism 126 of the base 102. For example, the attachment mechanism 137 may include one or more hook-and-loop type fasteners such as fasteners 134 which may releasably couple to corresponding fasteners 127 of the base 102 so as to couple the positioner 104 to the base 102 in a desired position. The fasteners 134 may include tabs 136 suitable for grasping by a user to decouple a corresponding fastener 134 from the corresponding fastener 127 of the base 102. The tabs 136 may extend past a periphery of the body 130 so that the tabs 136 may be easily grasped. However, it is also envisioned that the tabs may be formed integrally with the body and the fasteners.

The fasteners 134 may be located adjacent to a corresponding end of the opposed ends 135. The positioner 104 may be coupled to the base 102 such that its position relative to a longitudinal axis (La) of the base 102 and may be adjustable described. Similarly, the positioner 104 may be coupled to the base 102 such that its height (h) relative to the base 102 may vary as described. For the sake of clarity, it may be assumed that the longitudinal axis (La) may be aligned with a z axis and the height (h) may be adjusted along a y axis such that a change in height may correspond with a change in the y axis). For the sake of clarity, it should be appreciated that the x, y, and z axes discussed herein regarding the system 100 may correspond with x, y, and z axes, respectively, of an MRI in which embodiments of the present system may be used.

In accordance with further embodiments of the present system, the positioner 104 may guide or otherwise assist in aligning the upper section 106 relative to the base 102 with respect to height and/or longitudinal location so as to position the upper section 106 in a desired location relative to the base 102.

The flanges 132 may be formed from a ridged or flexible material as suitably applied and may be located adjacent to, or close by, a corresponding one of the opposed edges 133 of the positioner 104. However, in yet other embodiments, it is envisioned that the flanges 132 may be located between the opposed edges 133. The flanges 132 may be formed integrally with, or separately from, the body 130 of the positioner 104 from the same of different materials. For example, one or more of the flanges 132 may be formed from a flexible rubber or plastic which may be coupled to the body 130 which may be formed from, for example, a clear plastic such as acrylic or polycarbonate. However, in yet other embodiments, the body 130 may be molded to integrally form one or more of the flanges 132, as may be desired.

It is envisioned that one or more portions of the positioner 104 such as the body 130 may be formed from any suitable material such as a plastic, etc. For example, the positioner 104 may be formed from a plastic such as an acrylic (e.g., Plexiglas™, etc.), a polycarbonate, etc. The plastic may include a thermoplastic, as desired. Moreover, the positioner 104 may be molded into a desired shape for a given OOI or may be flat and may be folded or bent by a user during use.

In accordance with further embodiments of the present system, the positioner 104 may be disposable. Further, the positioner 104 may be shaped, sized, and/or landmarked (as described herein) in accordance with a desired use or application(s) intended for the positioner 104. When folded or otherwise bent, the body 130 may gain rigidity so as to be capable of supporting the upper section 106 during use, as configured. Accordingly, the body 130 may be formed from a thin sheet of material having a rigidity that may be enhanced when arched (e.g. folded or otherwise bent) during use. In accordance with embodiments of the present system, a biasing member (e.g., a semi-coiled wire spring) may be coupled to the positioner 104 to provide a biasing force to hold the positioner 104 in a desired shape, if so configured. The biasing member may, for example, be situated within a corresponding flange 132.

The upper section 106 may include one or more of a body 140 and an RF coil array 142 coupled to the body 140. The body 140 may include bottom ends 145, opposed edges 143, and an interior wall 147 defining a central chamber 141. The central chamber 141 may define at least part of the imaging volume in which the OOI may be situated for scanning. The upper section 106 may contact the positioner 104 such that the height and/or longitudinal position of the upper section 106 relative to the base 102 may be determined by a position and/or orientation of the positioner 104 relative to the base 102.

In accordance with embodiments of the present system, the upper section 106 may be situated between the flanges 132 of the positioner 104. However, it is also envisioned that the positioner 104 and/or the upper section 106 may include a guide track (e.g., a rail and/or slot) which may control the position of the upper section 106 relative to the positioner 104. Although a single side is shown, the opposite side of the system 100 may be similar to the side shown or altered depending on an intended use.

Figure 2A:
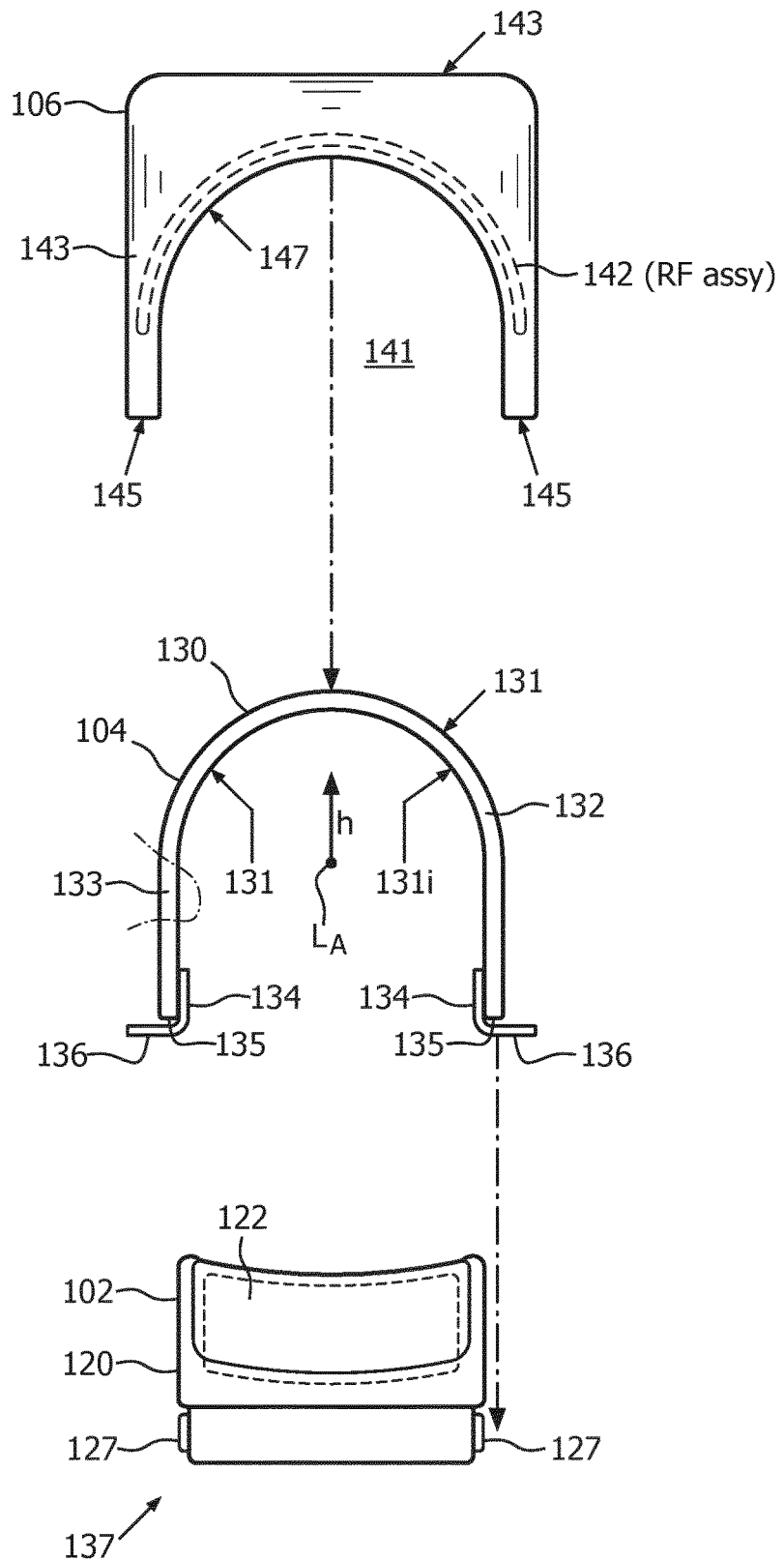
FIG. 2A shows a partially cutaway exploded end view of a portion of the RF coil system similar to that shown in FIG. 1 in accordance with embodiments of the present system.

FIG. 2A shows a partially cutaway exploded end view of a portion of the RF coil system 200 in accordance with embodiments of the present system. The fasteners 134 may be coupled to one of the major surfaces 131 of the body 130 such as an interior major surface 131$i$ of the major surfaces 131 using any suitable method such as adhesives, etc., as described. The tabs 136 of the fasteners 134 may extend beyond an outer periphery of the body 130 of the positioner 104. In accordance with embodiments of the present system, the positioner 104 may be formed of a ridged material such as a translucent or semi-translucent plastic material. In these embodiments, the positioner 104 is configured and/or otherwise formed to accommodate the OOI, such as to surround a knee (e.g., on three sides), when the positioner 104 is formed such as a portion of a knee coil. Although a single end is shown, the opposite end of the system 100 may be similar or different as desired and/or based on a given application.

Figure 2B:
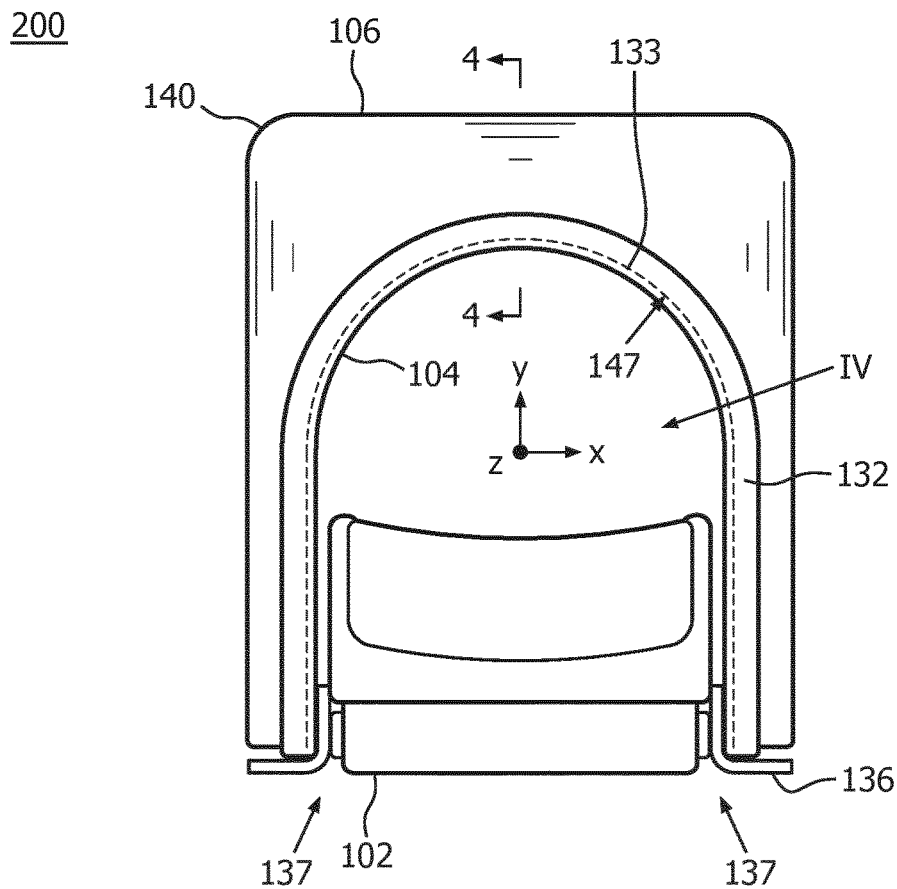
FIG. 2B shows a partially cutaway end view of a portion of the RF coil system similar to that shown in FIG. 1 in accordance with embodiments of the present system.

FIG. 2B shows a partially cutaway end view of a portion of the RF coil system 200 in accordance with embodiments of the present system. The system 100 is shown in a position suitable for performing a scanning operation in which the base 102 and/or the upper section 106 may define at least part of the imaging volume (IV) in which an OOI (not shown for the sake of clarity) such as a knee and/or other body part of a patient may be placed for scanning. The positioner 104 may be situated adjacent to the OOI such that it may be between at least a portion of the OOI and the interior wall 147 of the body 140.

Further, in embodiments when provided, RF coil arrays within the base 102, the positioner 104 and/or the upper section 106 may be in substantially perpendicular arrangement relative to each other or otherwise fixedly aligned relative to each other during positioning. For example, in accordance with embodiments of the present system, as a result of complementary structures on one or more of the base 102, the positioner 104 and/or the upper section 106, the position of the RF coils arrays are provided in a fixed relation to each other. In this way, problems in aligning the one or more coils to each other and/or the OOI that exist in prior systems are alleviated.

Figure 2C:
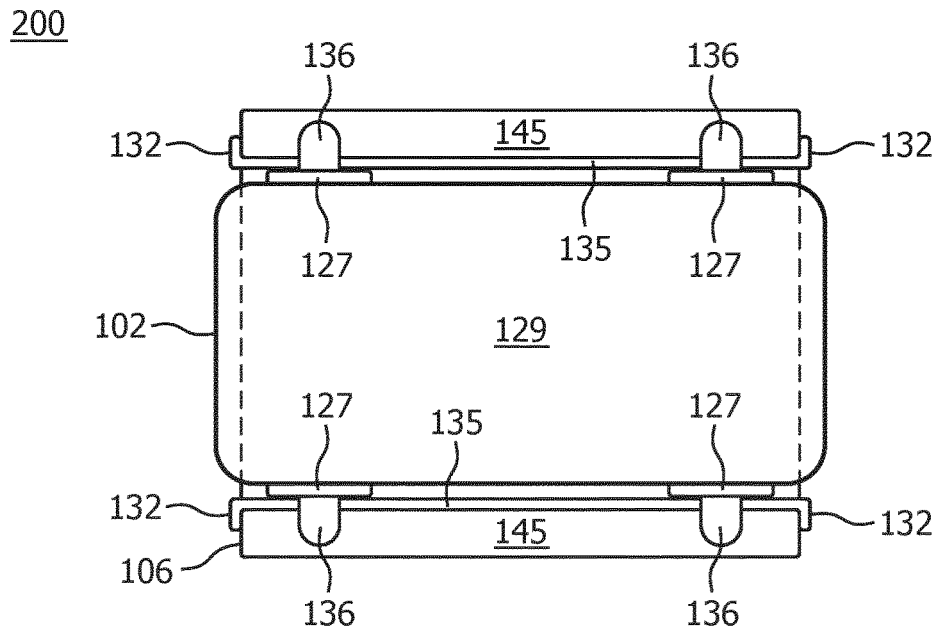
FIG. 2C shows a bottom view of a portion of the RF coil system similar to that shown in FIG. 1 in accordance with embodiments of the present system.

FIG. 2C shows a bottom view of a portion of the RF coil system 200 similar to that shown in FIG. 1 in accordance with embodiments of the present system. The body 120 of the base 102 may include a bottom cover 129. The bottom cover 129 may seal the at least one cavity (e.g., see, 128, FIG. 1) of the base 102. The bottom cover 129 may include mounting pads as desired for example to prevent, and/or reduce undesirable movement during use, assist in positioning the OOI, and/or otherwise aid in positioning and/or comfort of the patient.

Figure 3A:
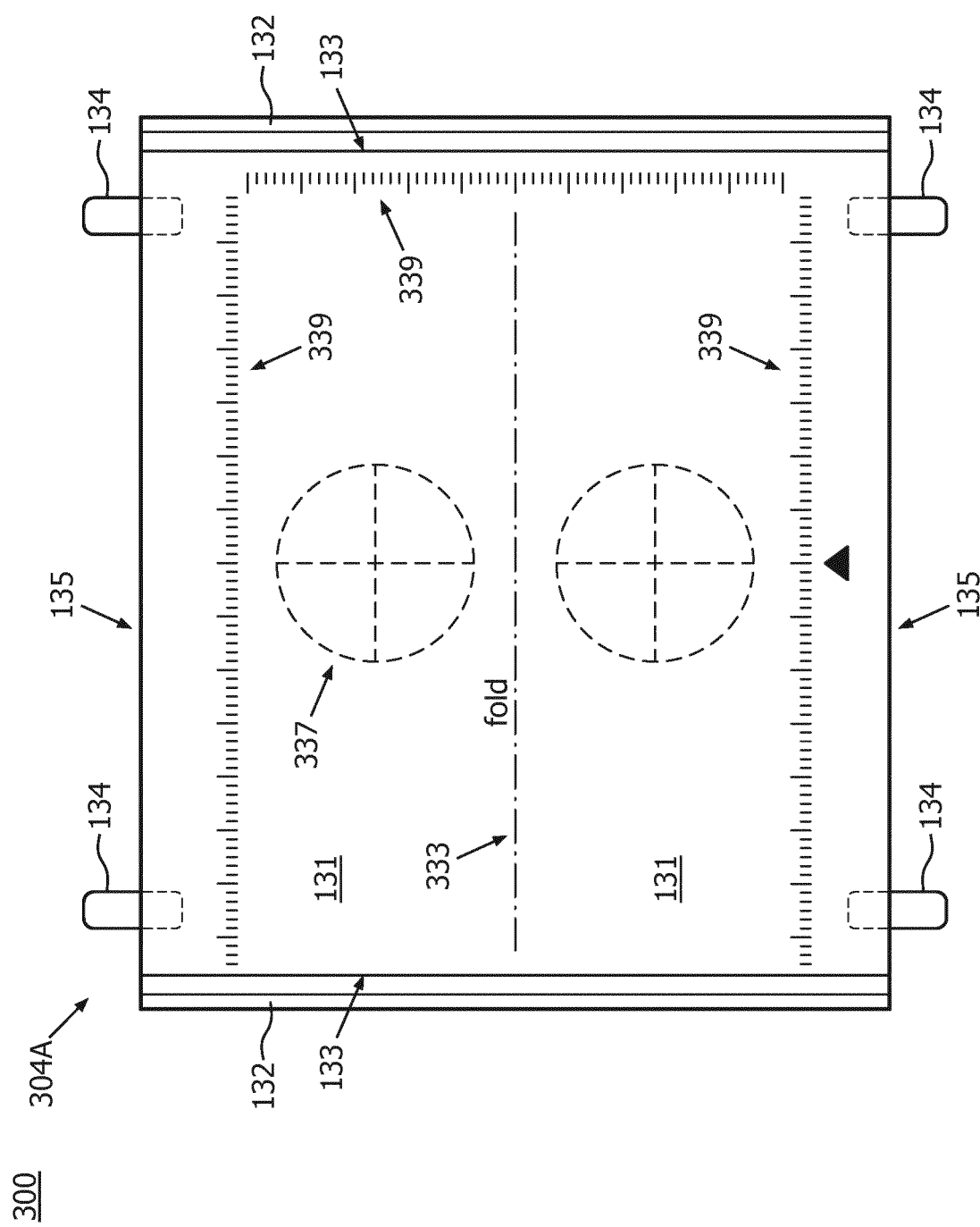
FIG. 3A shows a top view of a portion of a positioner in a flattened position in accordance with embodiments of the present system.

FIG. 3A shows a top view of a portion of a portion of the RF coil system 300 in accordance with embodiments of the present system including a positioner 304A in a flattened position in accordance with embodiments of the present system. The positioner 304 may be similar to the positioner 104 and similar numerals may have been used to denote similar portions thereof.

In accordance with embodiments of the present system, the positioner 304 may include landmarks such as graphics 337 which a user such as a clinician may use to properly align the positioner 304 with regard to the OOI and/or other portions of the system. The landmarks, may include any suitable graphics, text, etching, notches, tabs, slots, etc., which may guide a user so that the user may locate the positioner 304 relative to an OOI and/or portions of the system. The landmarks may further illustrate to a user a direction in which the positioner 304 may be bent for use, in an embodiment wherein the positioner 304 is flexible and/or otherwise not initially formed with a bend. The landmarks may include graphics such as a rule 339 and/or other graphics that a user may use to align the positioner 304 relative to the OOI and/or the base 102 and/or portions thereof. Further, a user may mark the positioner 304 using a marker (erasable or non-erasable) as may be desired.

The landmarks may further include instructions for desired uses (e.g., "for a knee scan, align knee positioning landmarks with corresponding portions of the knee," "for a shoulder scan, align shoulder positioning landmarks with corresponding portions of the shoulder," for an arm scan, align arm positioning landmarks with corresponding portions of the arm," etc.). In accordance with further embodiments of the present system, the positioner 304 may be flexible such that it may be flexibly formed around the OOI during setup. As readily appreciated, the shape of the positioner 304 still complements the shape that of the base and the upper section as described.

In accordance with embodiments of the present system, the positioner 304 may be folded, bent, rolled, etc., each term and other variations used herein for example, however should be understood to encompass other configurations of the present system, wherein the positioner is otherwise formed to the OOI at the time that the positioner is placed around the OOI (e.g., formed along line 333 as described herein). In one or more of these embodiments, the positioner 304 may be stored in a flattened orientation as desired and shown. In an embodiment wherein the positioner 304 is rollable, the positioner 304 may be stored in many shapes as desired. Other characteristics of a positioner such as the positioner 304 are descried herein with reference to further figures.

Figure 3B:
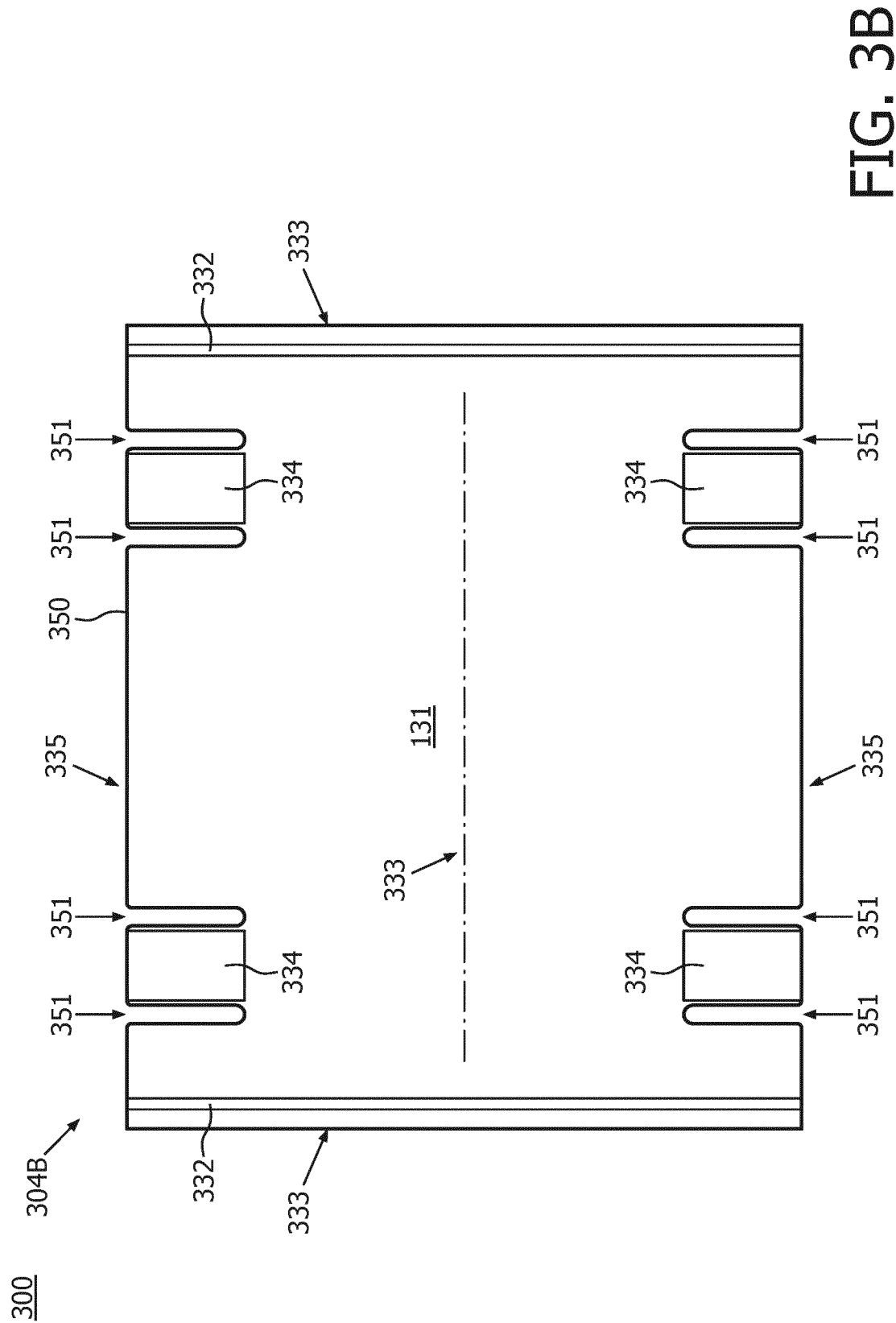
FIG. 3B shows a top view of a portion of a positioner in a flattened position in accordance with embodiments of the present system.

FIG. 3B shows a top view of a portion of a portion of the RF coil system 300 including a positioner 304B in a flattened position in accordance with embodiments of the present system. The positioner 304B may be similar to the positioner 304 and similar numerals may have been used to denote similar portions thereof. However, the positioner 304B may include notches 351 cut into a body 350 of the positioner 304B on either side of fasteners 334 that are attached to the body 350. Further, flanges 332 may be located slightly away from adjacent ends 333. The notches 351 may include any suitable cut which may separate the body 350 along the cut. Further, the notches 351 may interrupt a periphery of opposed ends 335.

Figure 4:
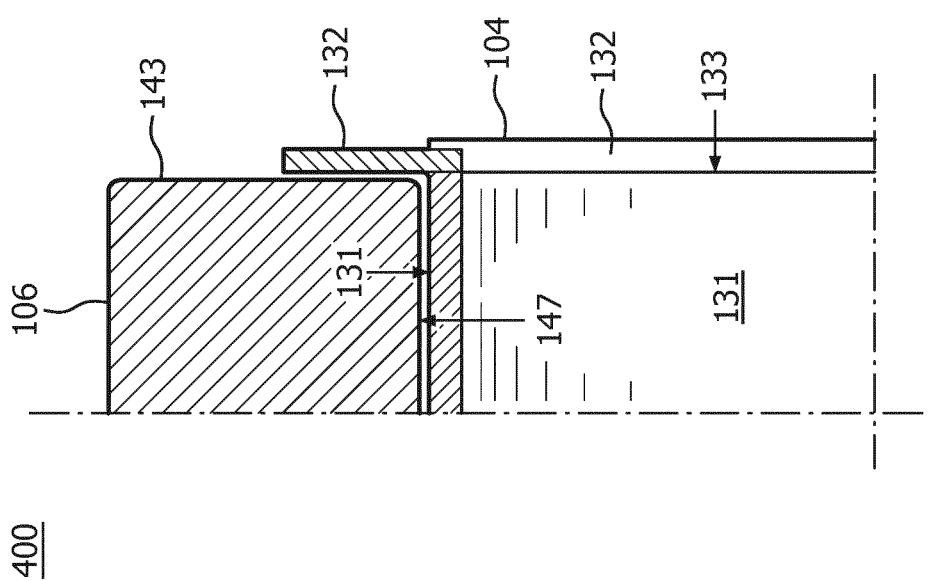
FIG. 4 shows a detailed cross-section view of a portion of a positioner and upper section of an RF coil system in accordance with embodiments of the present system.

FIG. 4 shows a detailed cross-section view of a portion of a positioner and upper section of an RF coil system 400 such as taken along lines 4-4 of FIG. 2B in accordance with embodiments of the present system. In the illustrative embodiment, the positioner 104 and the upper section 106 of the RF coil system 100 is shown. In accordance with embodiments of the present system, longitudinal alignment (e.g., along the La) of the upper section 106 relative to the base (e.g., 102) may be controlled by the flanges 132 of the positioner 104 which may contact opposed edges 143 so as to guide the upper section 106 into a desired position (alignment) relative to the base. Further, height (h) of the upper section 106 relative to the base 102 may be controlled by the interior wall 147 of the upper section 106 contacting an adjacent major surface 131 of the positioner 104.

Figure 5:
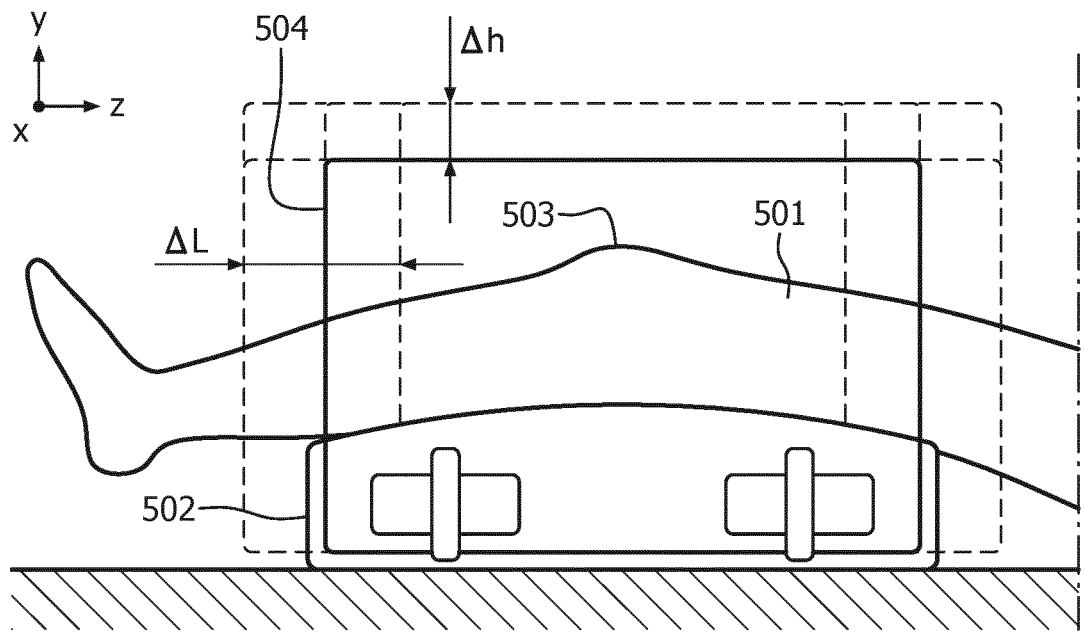
FIG. 5 shows a side view of a range of motion of a positioner relative to a base in accordance with embodiments of the present system.

FIG. 5 shows a side view of an RF coil system 500 including a range of motion of a positioner 504 relative to a base 502 in accordance with embodiments of the present system. The positioner 504 and the base may be similar to the positioner 104 and the base 102, respectively. An OOI such as a knee 503 of a patient 501 is shown for the sake of clarity. Lateral position and height of the of the positioner 504 may varied relative to the base 504 as illustrated by ΔL (e.g., change along the longitudinal axis) and Δh (e.g., change along the y axis), respectively. In accordance with embodiments of the present system, this may provide for desired alignment of an upper cover relative to the base. Further, in accordance with embodiments of the present system, as described the positioner may change height from the base, for example to accommodate different patient sizes (e.g., to accommodate an adult and a child).

Figure 6:
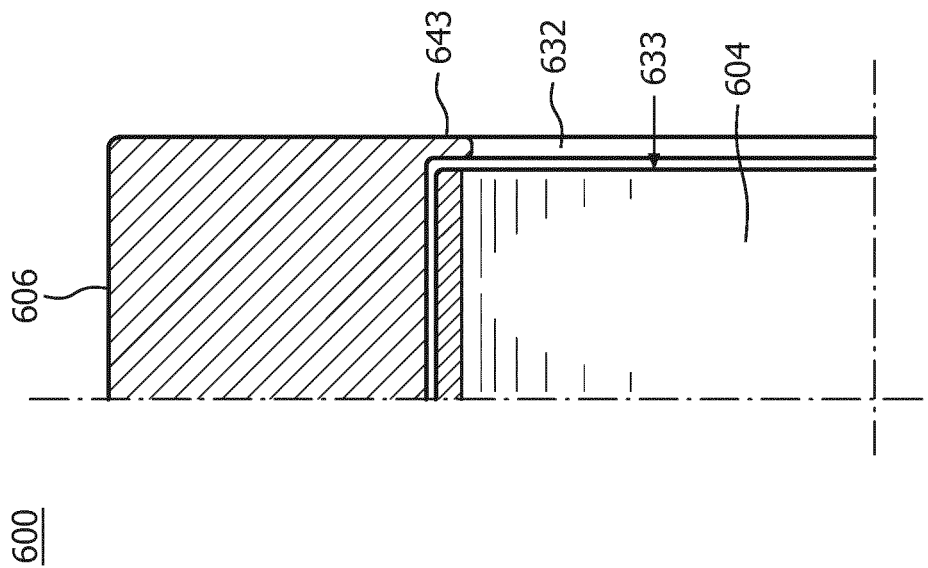
FIG. 6 shows a detailed cross-section view of a portion of the positioner and an upper section in accordance with embodiments of the present system.

FIG. 6 shows a detailed cross-section view of an RF coil system 600 including a portion of a positioner 604 and an upper section 606 in accordance with embodiments of the present system. The positioner 604 and the upper section 606 may be similar to the positioner 104 and the upper section 106, respectively. However, the upper section 606 may include a flange 632 located at each opposed edge 643 (only one of which is shown for the sake of clarity) and the positioner 604 may include opposed edges 633 (only one of which is shown for the sake of clarity) which may lack flanges. The flange 632 may contact an adjacent one of the opposed edges 633 to guide the upper section 606 into alignment during use. In accordance with yet other embodiments, other types of guides may be suitably utilized to position upper section relative to the positioner and/or the positioner relative to the base.

Figure 7:
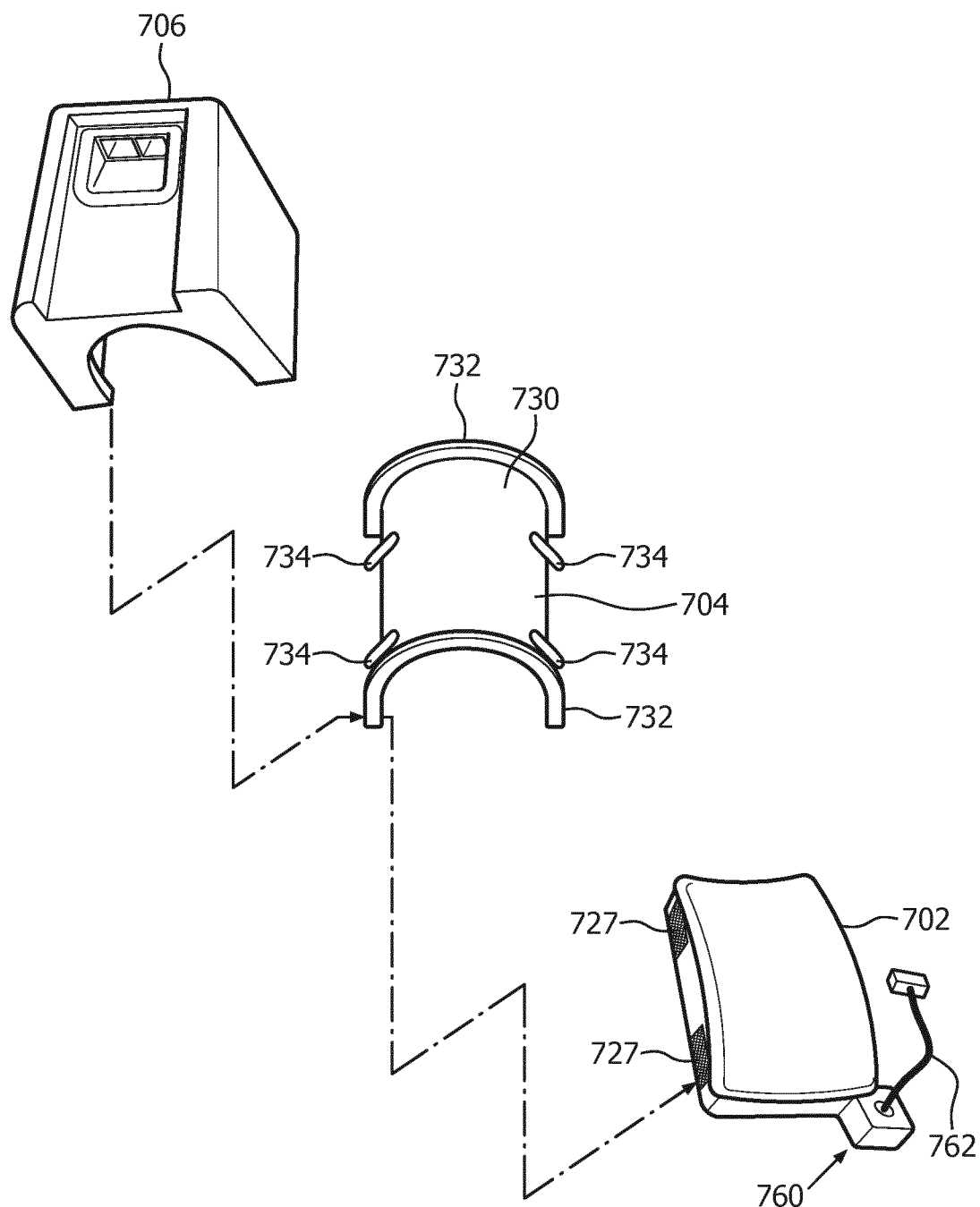
FIG. 7 shows an exploded perspective end view of a portion of an RF coil system operating in accordance with embodiments of the present system.

FIG. 7 shows an exploded perspective end view of a portion of an RF coil system 700 (hereinafter system 700 for the sake of clarity) operating in accordance with embodiments of the present system. The system 700 may be similar to the system 100 and may include one or more of a base 702, a positioner 704, and an upper section 706 that may be similar to the base 102, the positioner 104, and the upper section 106, respectively, of the system 100. In accordance with embodiments of the present system, the base 702 may include a distal end 760 and a communication link such as a wireless link 762 for external communication (e.g., with an MRI control system, etc.).

The positioner 704 may include a body 730 and flanges 732, the latter of which may act as guides to align the upper section 706 relative to the positioner 704 and/or the base 702. The positioner 704 may include a fastener system such as a hook-and-loop type fasteners 734 which may couple to corresponding hook-and-loop fasteners 727 of the base 702. The fasteners may be shaped, sized, and/or positioned relative to the base 702 and/or the positioner 704 so that a desired change along a longitudinal axis and a desired change in height of the positioner 704 relative to the base 702 may be accommodated and secured.

Figure 8A:
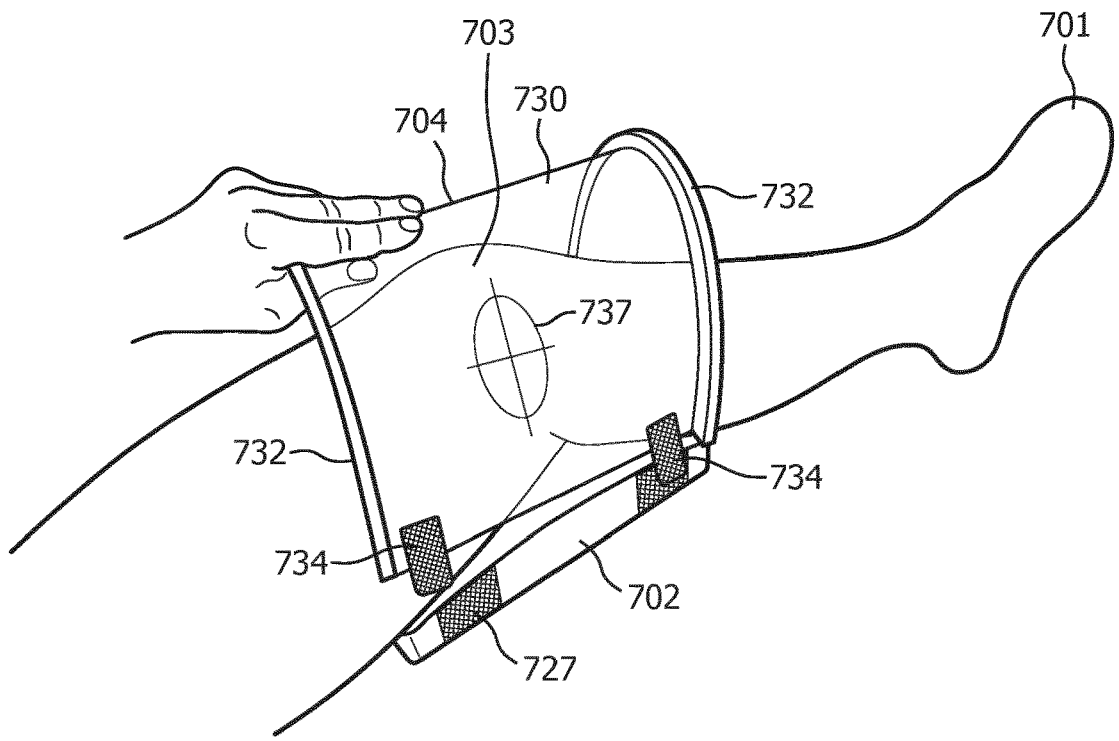
FIG. 8A shows a perspective font side view of a portion of the RF coil system in which a positioner is being positioned about a knee of a patient in accordance with embodiments of the present system.
Figure 8B:
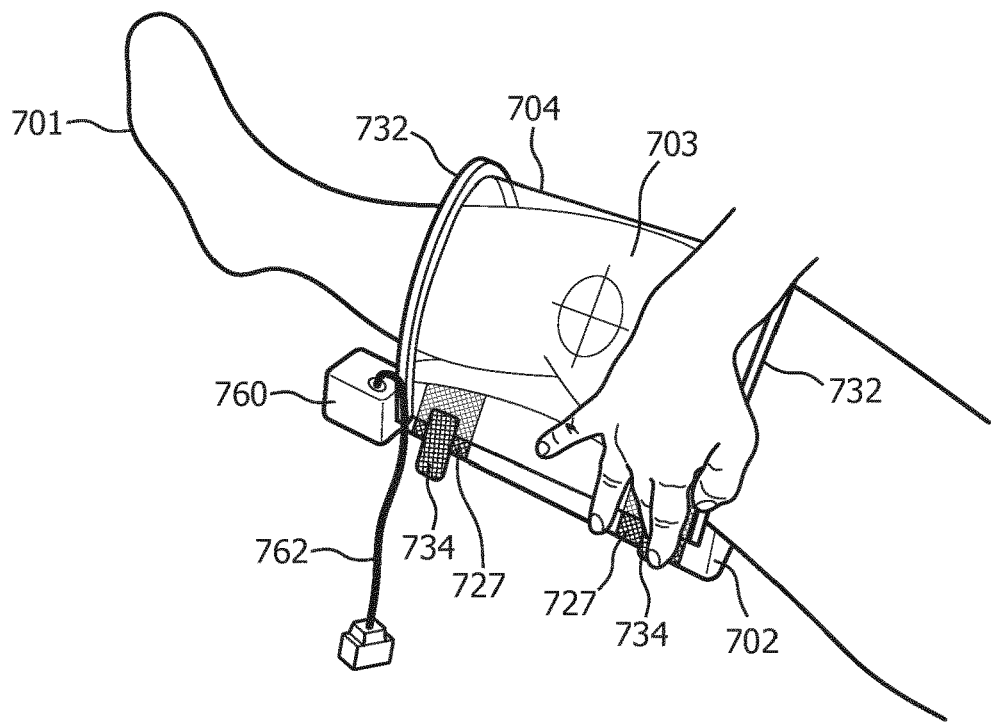
FIG. 8B shows a perspective rear side view of a portion of the RF coil system in which the positioner is positioned about the knee of the patient in accordance with embodiments of the present system.
Figure 8C:
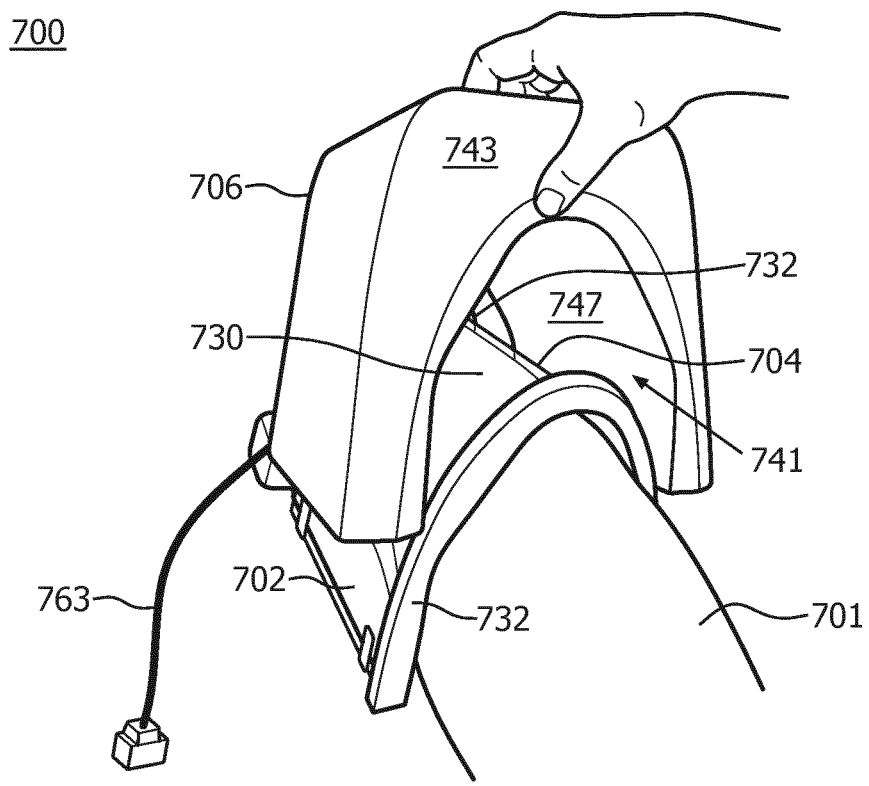
FIG. 8C shows a perspective rear end view of a portion of the RF coil system in which an upper section is being positioned over a positioner and a knee of a patient in accordance with embodiments of the present system.
Figure 8D:
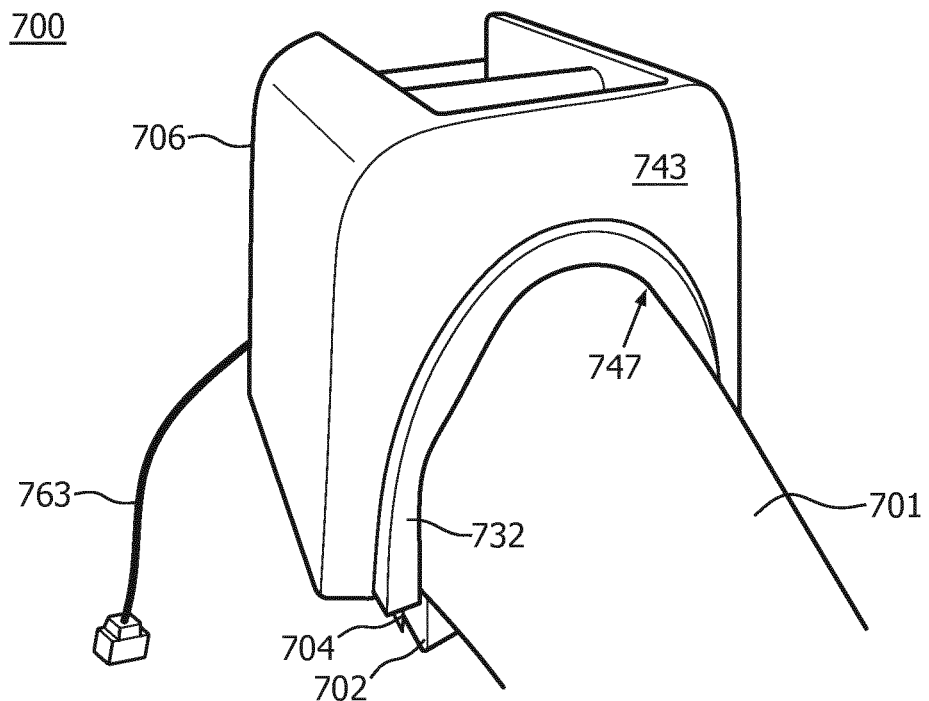
FIG. 8D shows a perspective rear end view of a portion of an RF coil system in which an upper section is positioned over a positioner and a knee of the patient in accordance with embodiments of the present system.
Figure 8E:
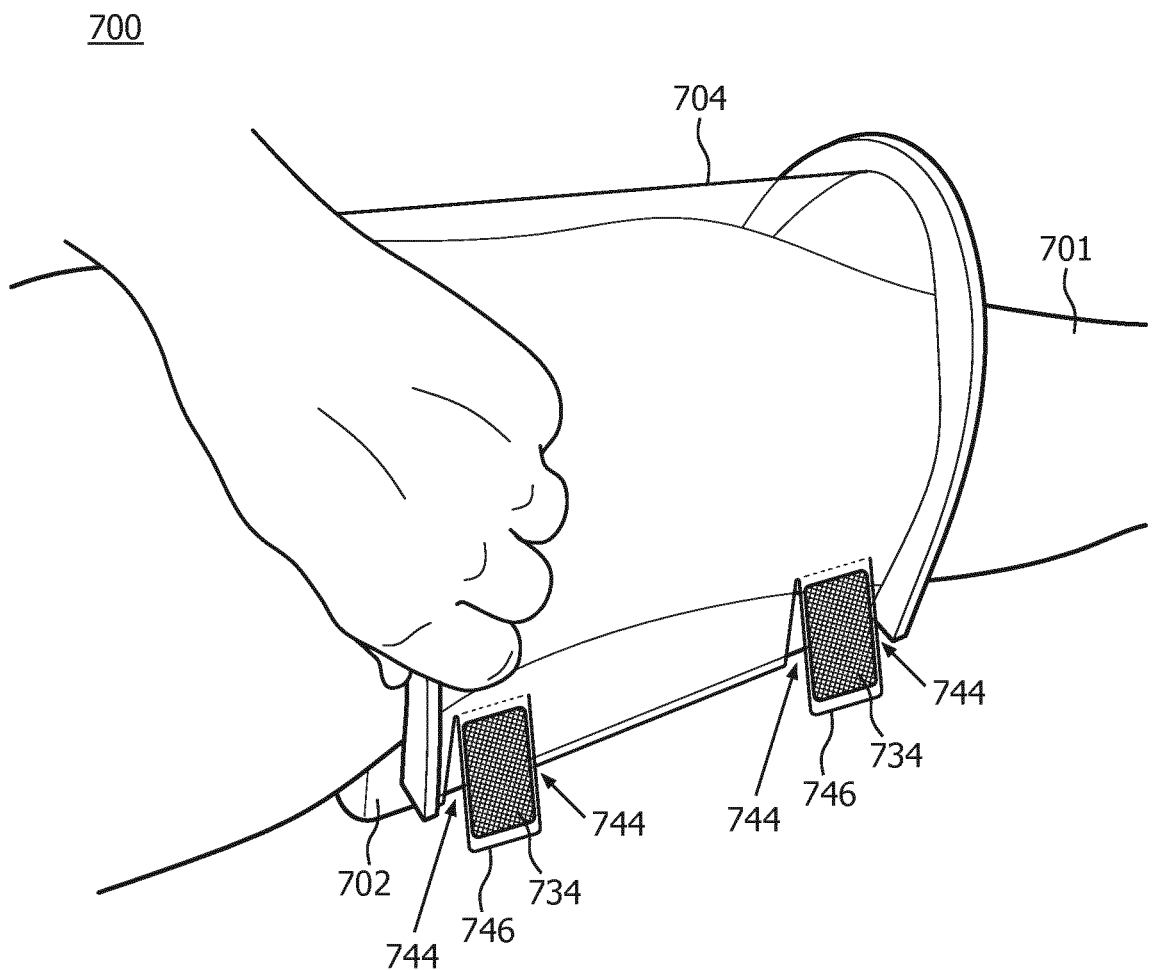
FIG. 8E shows a perspective front side view of a portion of an RF coil system in which a positioner is being removed from a base in accordance with embodiments of the present system.

A process of setting up the system 700 to perform a scan of a knee of a patient is described with reference to FIGS. 8A through 8E, and 10A through 10D wherein: FIG. 8A shows a perspective font side view of a portion of the RF coil system 700 in which the positioner 704 is being positioned about a knee 703 of a patient 701 in accordance with embodiments of the present system; FIG. 8B shows a perspective rear side view of a portion of the RF coil system 700 in which the positioner 704 is positioned about the knee 703 of the patient 701 in accordance with embodiments of the present system; FIG. 8C shows a perspective rear end view of a portion of the RF coil system 700 in which the upper section 706 is being positioned over the positioner 704 and the knee 703 of the patient 701 in accordance with embodiments of the present system; FIG. 8D shows a perspective rear end view of a portion of the RF coil system 700 in which the upper section 706 is positioned over the positioner 704 and the knee 703 of the patient 701 in accordance with embodiments of the present system; and FIG. 8E shows a perspective front side view of a portion of the RF coil system 700 in which the positioner 704 is being removed from the base 702 in accordance with embodiments of the present system.

With reference to FIG. 8A, the positioner 704 may be placed about the base 702 and an OOI such as a knee 703 of a patient 701. The positioner 704 may be aligned relative to the knee 703 using landmarks 737 such as crosshairs, etc. Once aligned, the hook-and-loop fasteners 734 of the positioner 704 may be situated about the base 702 and the OOI so as to align the positioner 704 in a desired position relative to the base 702. In accordance with embodiments of the present system, hook-and-loop fasteners 734 of the positioner 704 may be secured to corresponding hook-and-loop fasteners 727 of the base 702 so as to secure the positioner 704 to the base 702 in a desired position. When aligned, the positioner 704 may snugly surround the OOI as may be desired.

With reference to FIG. 8B, the user is shown engaging hook-and-loop fasteners 727 and 734 to each other so as to secure the positioner 704 relative to the base 702. In accordance with embodiments of the present system, the wired link 762 may extend from the distal end 760 and may be configured for wireless coupling to an external communication system, such as wireless communication system, as desired.

With reference to FIG. 8C, once the positioner 704 is aligned and secured to the base 702, the upper section 706 may be slid over the positioner 704. In accordance with embodiments of the present system, the upper section 706 and may be guided by an exterior surface of the body 730. Further, the upper section 706 may be guided by the flanges 732 which may engage corresponding opposed edges 743 of the upper section 706. Accordingly, the positioner 704 may guide the upper section 706 into a desired position relative to the base 702. The upper section 706 may include an interior wall 747 defining a central chamber 741. The upper section 706 may include a wired and/or wireless (e.g., radio frequency, fiber optic, etc.) link 763 which may be coupled to an external communication port or to a port on the base 702, as desired. In accordance with embodiments of the present system, the base 702 may operate to couple signals from the link 763 to the link 762 so as to form a piggy back connection and/or otherwise couple a connection from the base 702 as desired.

With reference to FIG. 8D, after sliding the upper section 706 over the positioner 704, the upper section 706 may be aligned in a desired position for scanning. The positioner 704 may support the interior wall 747 of the upper section 706 so as to control height and/or orientation of the upper section 706 in relation to the base 702. The opposed edges 743 of the upper section 706 may be situated between the flanges 732 (only one of which is shown).

In accordance with embodiments of the present system, an arched shape to the positioner 704 may enhance rigidity of the positioner. Further, as the shape of the interior wall 747 of the upper section 706 corresponds with the arched shape of the interior wall 747, when in contact it may further enhance the rigidity of the positioner 704. Further, in accordance with embodiments of the present system, the interior wall 747 may engage the hook-and-loop fasteners 734 and 727 of the positioner 704 and the base 702, respectively, so as to maintain the coupling between these fasteners.

With reference to FIG. 8E, in accordance with embodiments of the present system, to remove the system 700 from the patient, the upper section 706 may be removed from the positioner 704. For example, corresponding hook-and-loop fasteners 734 and 727 may be decoupled from each other. The positioner 704 may include slots 744 which may be similar to the slots 351 shown in FIG. 3B. These slots 744 may define tabs 746 suitable for grasping by a user to decouple corresponding hook-and-loop fasteners 734 and 727 each other. Further, a body 730 of the positioner 704 may provide a biasing force to bias the hook-and-loop fasters 734 away from the body 702 so as to avoid unintentional attachment between the hook-and-loop fasters 734 of the positioner 704 and the hook-and-loop fasters 727 of the body 702 during installation.

Figure 9:
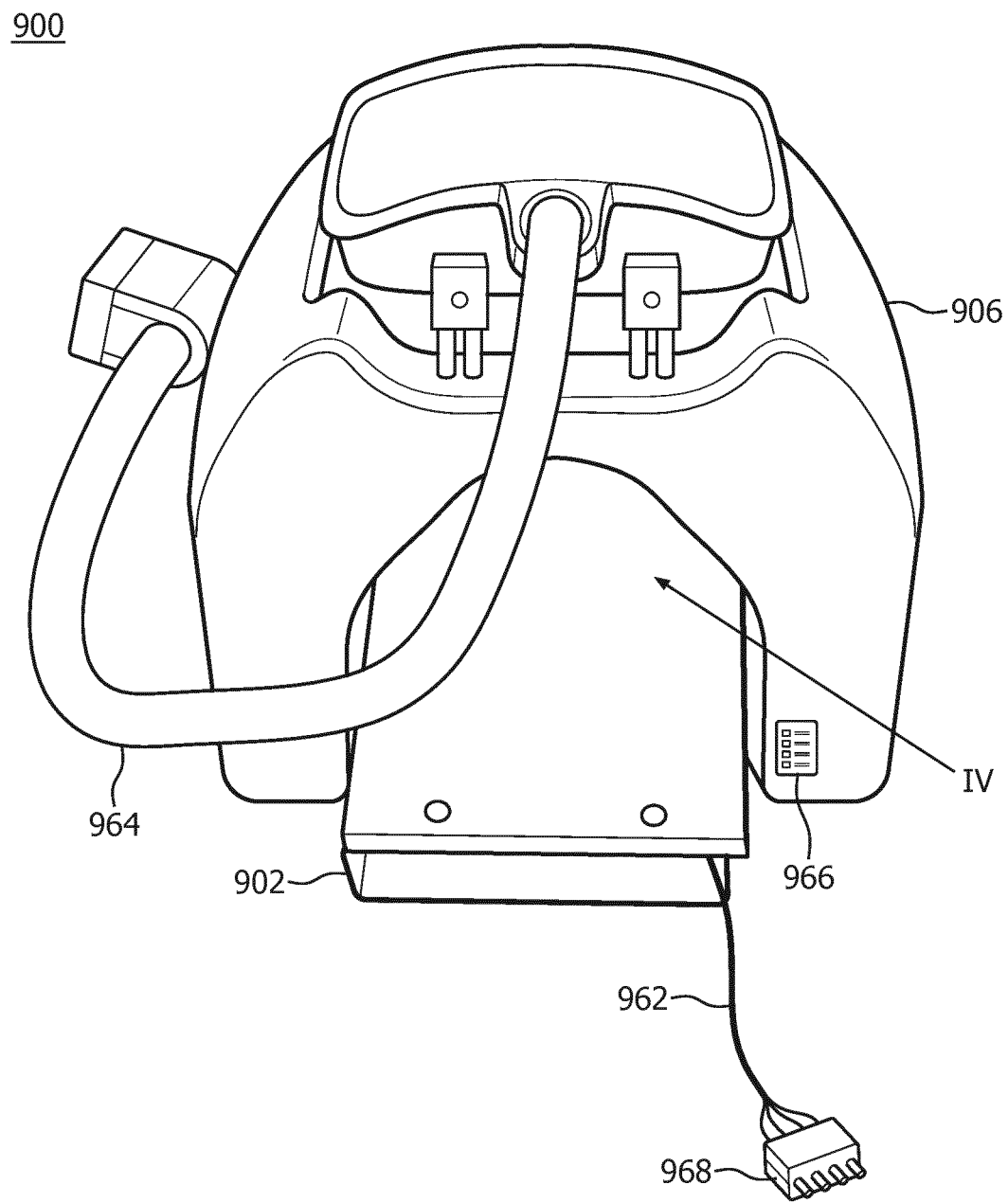
FIG. 9 shows a partially cutaway perspective top end view of an RF coil system in accordance with embodiments of the present system.

FIG. 9 shows a partially cutaway perspective top end view of an RF coil system 900 (hereinafter system 900 for the sake of clarity) operating in accordance with embodiments of the present system. The system 900 may be similar to one or more of the other systems and may include one or more of a base 902, a positioner, and an upper section 906. The system 900 is shown in a position suitable for performing a scanning operation. Accordingly, the base 902 together with the positioner and/or the upper section 906 may define at least part of the imaging volume (IV) in which an OOI (not shown for the sake of clarity) may be placed for scanning. In accordance with embodiments of the present system, a link 964 may be coupled to an external system controller to enable communication between the external system controller (e.g., an MRI system controller) and the RF coil system 900. Accordingly, image information in any suitable format (e.g., raw, digitized, reconstructed, etc.) may be transmitted to the external system controller for further processing. Further, operating commands and/or instructions may be received from the external system controller. The base 902 may be piggy backed to the upper section 906 via a link 962 (such as a wired link) so as to enable communication between the base 902 and the upper section 906 and therefore the external system controller. More particularly, the link 962 may include a coupler 968 which may couple to the upper section 906 using any suitable method such as via a port 966.

In accordance with some embodiments, the upper section may be coupled to the base, positioner and/or to the external system controller to enable communication using any suitable wired and/or wireless coupling method. Further, it is envisioned that the upper section may be physically coupled to the base using for example a sliding-type coupling or otherwise as desired.

In accordance with embodiments of the present system, the system may be shaped and sized such that alignment of the base and the upper section may be performed by fixing the upper section at a height which would allow the smallest knee envisioned to be precisely imaged when a bottom end (e.g., see, 145) of the upper section hits a table surface and then permit the upper section to otherwise rest on the positioner. The system may further include padding which may be integrated with the base, positioner and/or upper section so as to provide comfort to a patient and/or absorb some weight of the RF coil array of the system while providing a small imaging volume. In accordance with embodiments, it is envisioned that the base and the positioner may provide for a larger OOI through adjustment of the positioner over the OOI and adjustment of the base.

Figure 10A:
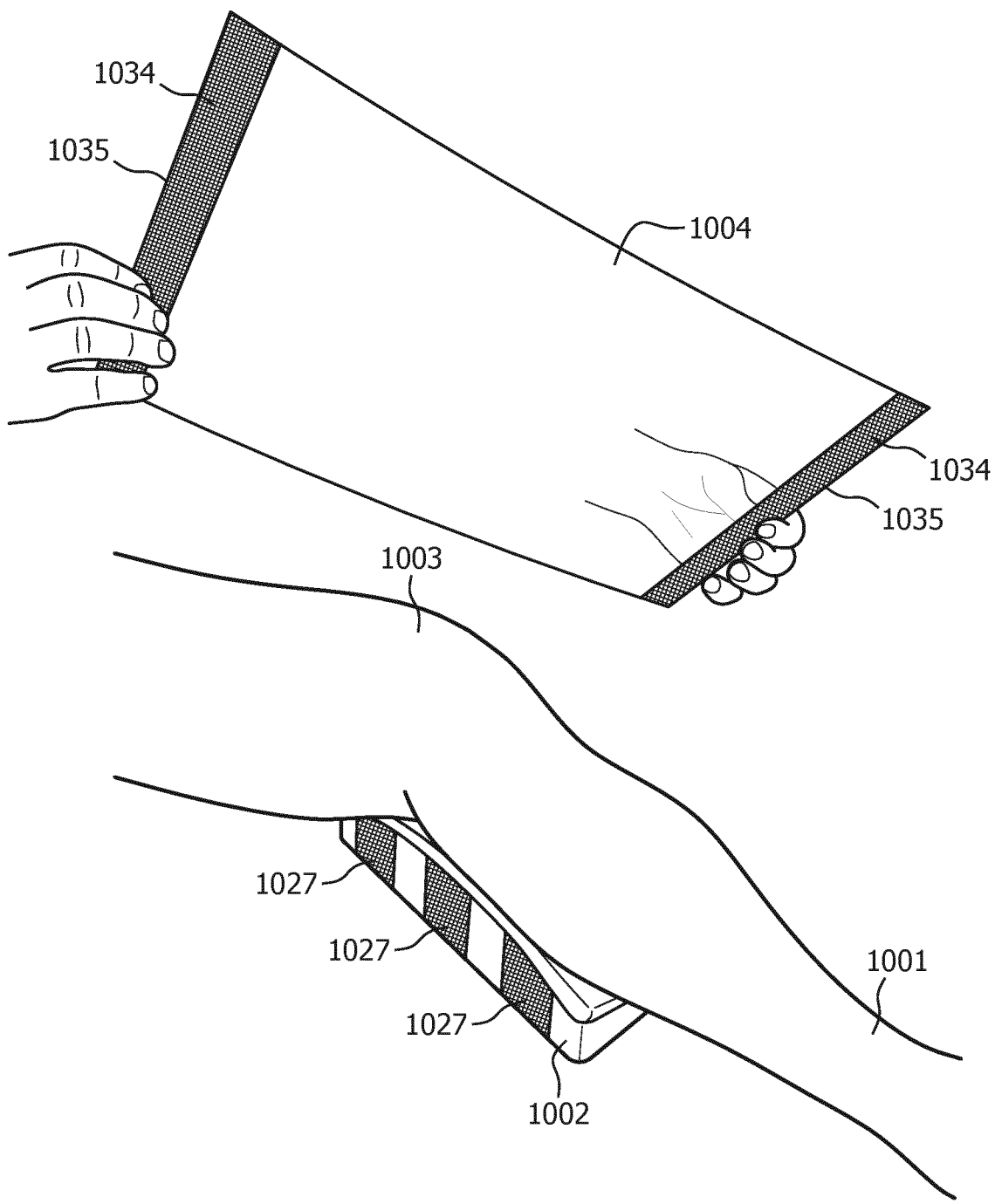
FIG. 10A shows a perspective top front side view of a portion of an RF coil system in which a positioner is being prepared to be positioned about a knee of a patient in accordance with embodiments of the present system.
Figure 10B:
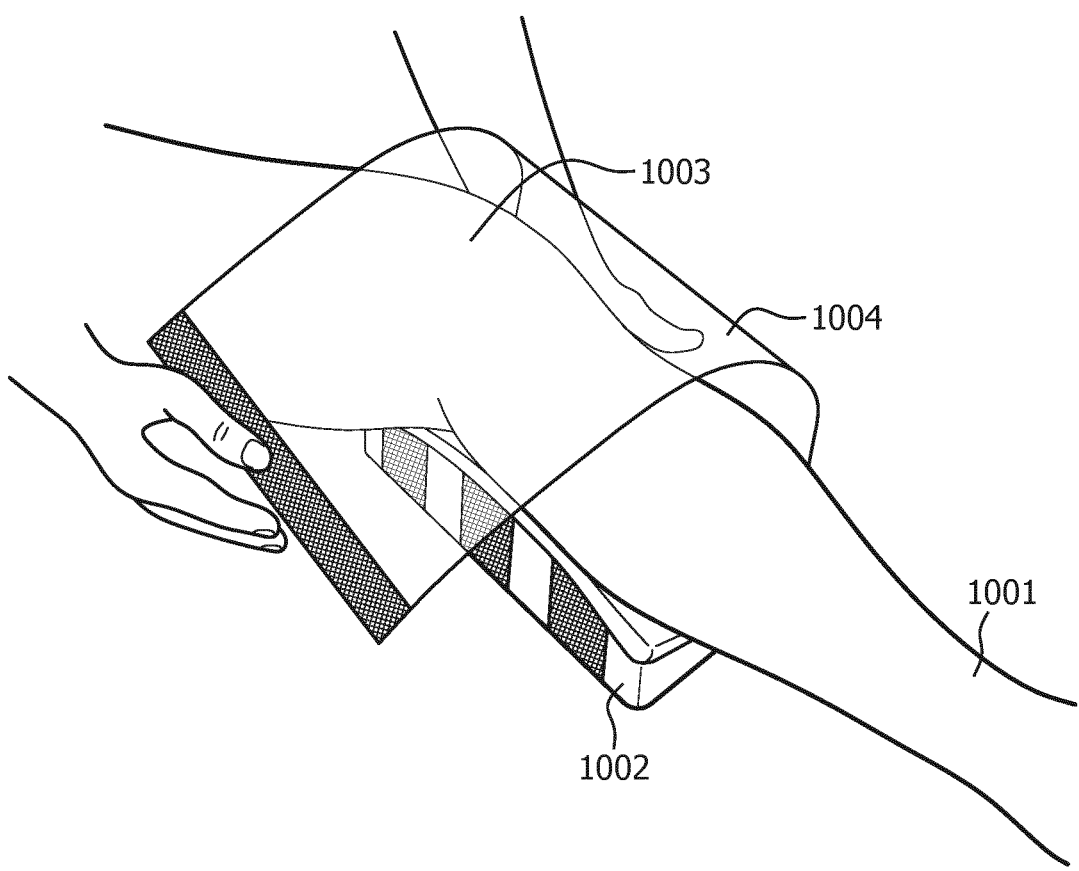
FIG. 10B shows a perspective top front side view of a portion of an RF coil system in which a positioner is initially positioned about a knee of a patient in accordance with embodiments of the present system.
Figure 10C:
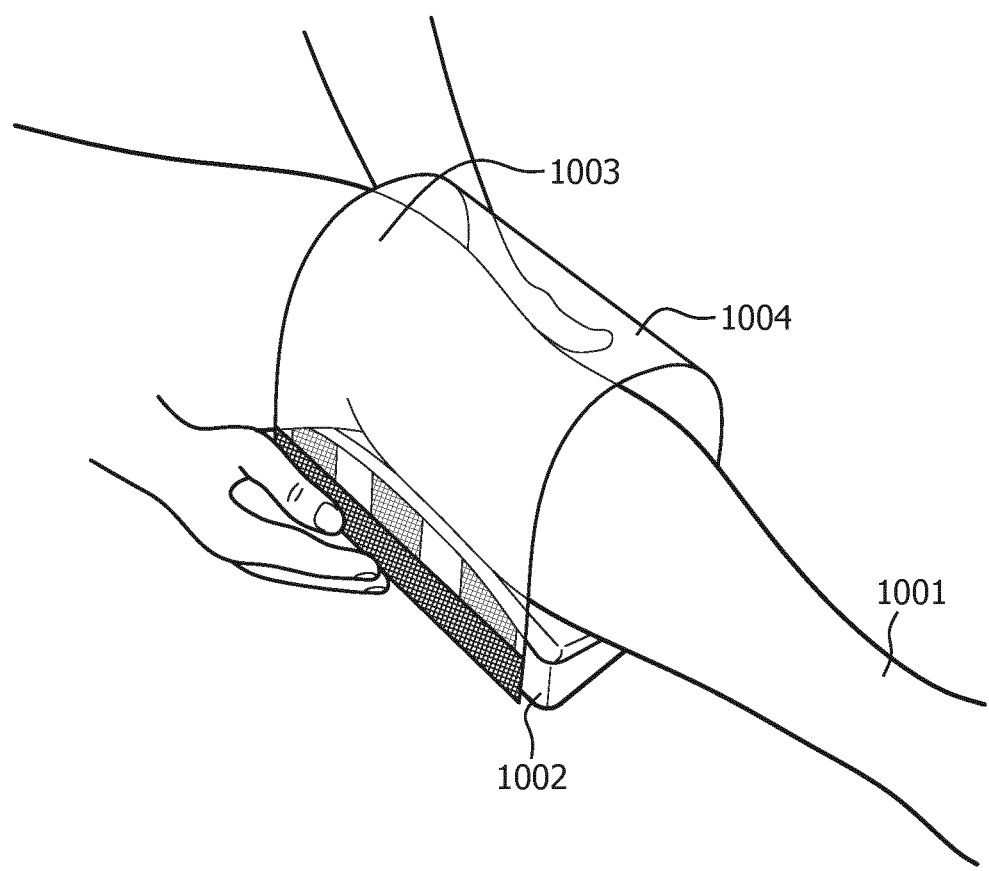
FIG. 10C shows a perspective top front side view a portion of an RF coil system in which a positioner is positioned about a knee of a patient in accordance with embodiments of the present system.
Figure 10D:
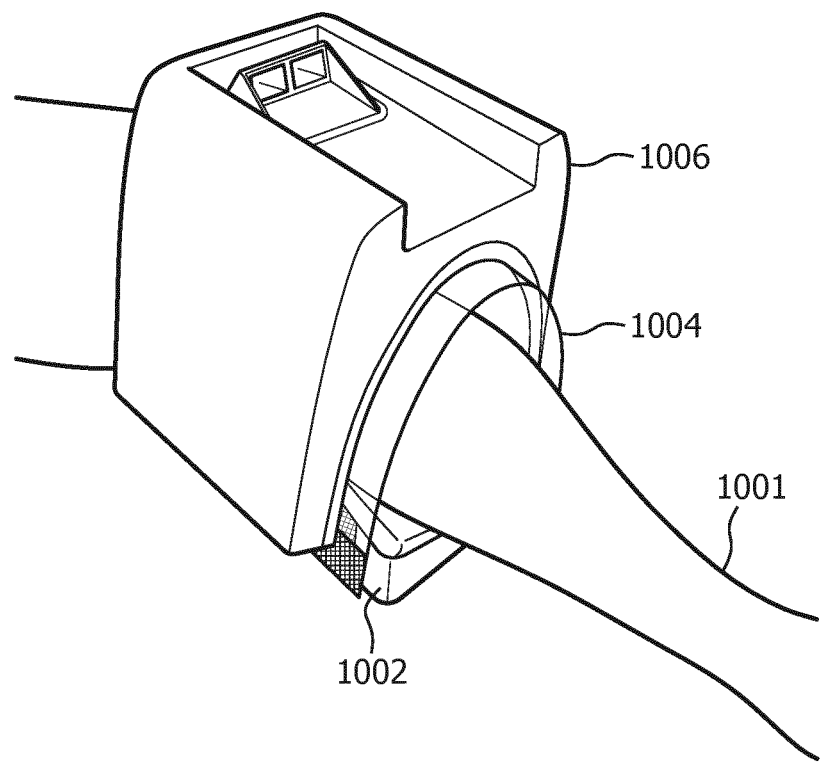
FIG. 10D shows a top front side view of a portion of a RF coil system in which an upper section is situated over a positioner in accordance with embodiments of the present system.

A process of setting up a system in accordance with embodiments of the present system to perform a scan of a knee of a patient is described with reference to FIGS. 10A through 10D utilizing a flexible positioner, wherein FIG. 10A shows a perspective top front side view of a portion of an RF coil system 1000 in which a positioner 1004 is being prepared to be positioned about a knee 1003 of a patient 1001 in accordance with embodiments of the present system; FIG. 10B shows a perspective top front side view of a portion of the RF coil system 1000 in which the positioner 1004 is initially positioned about the knee 1003 of the patient 1001 in accordance with embodiments of the present system; FIG. 10C shows a perspective top front side view of a portion of the RF coil system 1000 in which the positioner 1004 is positioned about the knee 1003 of the patient 1001 in accordance with embodiments of the present system; and FIG. 10D shows a perspective top front side view of a portion of the RF coil system 1000 in which an upper section 1006 is situated over the positioner 1004 in accordance with embodiments of the present system.

Referring to FIG. 10A, the positioner 1004 may be similar to the positioner 104. However, in accordance with embodiments of the present system, the positioner 1004 may include a continuous hook-and-loop fastener 1034 portion (e.g., a loop portion of a hook and fastener system) at each of opposed ends 1035 of the positioner 1004. Further, the base 1002 may include a plurality of hook-and-loop fastener 1027 portions (e.g., hook portions of a hook and fastener system) on opposed front and rear sides thereof.

In use, an OOI such as a knee 1003 of a patent 1001 may be placed over the base 1002 and the positioner 1004 may be prepared to be wrapped about the OOI (e.g., the knee 1003) and thereafter attached to the base 1002 as illustrated in FIGS. 10B and 10C. Thereafter, an upper portion 1006 may be placed over the positioner 1004 as shown in FIG. 10D such that it may be guided and supported by the positioner 1004 via the base 1002 depending upon height settings. The arched shape of the positioner 1004 may enhance rigidity of the (flexible) positioner 1004 so that it may support the upper portion 1006. As appreciated, though the positioner may be flexible in these embodiments, it may be formed somewhat as a sheet. In this way, as the positioner is formed around a length of the OOI, the rigidity of the positioner for example in a plane perpendicular to the length of the OOI may be greatly increased as compared to when the positioner is for example, laid flat. In this way, problems with prior system are alleviated in that the weight of the coil need not be supported by the knee and is supported or somewhat supported by the positioner. In accordance with embodiments of the present system, the system 1000 may then be ready for MR acquisition.

Accordingly, embodiments of the present system may provide a positioner which supports an anterior (e.g., upper portion) RF receiver coil over a desired OOI (e.g., anatomy of a patient) for scanning without placing pressure or weight on the patient. An attachment mechanism may provide for the adjustment of the positioner relative to a posterior (e.g., base) portion that may include an RF receiver coil. The positioner may be transparent so that a user such as a clinician may easily and accurately determine how to place the positioner relative to the OOI for scanning so that it may be aligned relative to the OOI. The positioner may be formed from a plastic sheet and, as such, may be extremely light and inexpensive so it can be easily replaced. The upper portion which may weigh considerably more than the positioner may be positioned after the positioner is aligned and attached to the base thereby simplifying a setup process. In accordance with embodiments, the positioner may also cover the patient surface side of the RF coil of the upper portion, thus cleaning the surface side of the RF coil of the upper portion may be simplified and less abusive as it need not be in contact with the patient at any time. Further, as the positioner in accordance with embodiments may not include any electronics, it can be easily cleaned or replaced. In accordance with embodiments of the present system, no adjustable joints need be utilized so setup is simplified and dangers of pinching the OOI may be eliminated.

Thus embodiments of the present system may provide a semi-rigid, anatomically shaped (coil) positioner formed from a thin, translucent, plastic shell having hook-and-loop fasteners (e.g., Velcro™ pads) adhered in desired locations to allow attachment to the opposing hook-and-loop fasteners adhered to posterior RF receiver coil housing. The hook-and-loop fasteners allow for adjustability in aligning and positioning of the (coil) positioner to make sure the anterior portion including a coil may be aligned properly over a desired OOI (e.g., desired patient anatomy) and in a position to keep pressure and weight off of the patient when the anterior portion is placed onto the positioner. The positioner and hook-and-loop fasteners may be further secured to a posterior portion (e.g., base) by a rigid housing (e.g., body) of the anterior portion as it is placed under the OOI.

Figure 11:
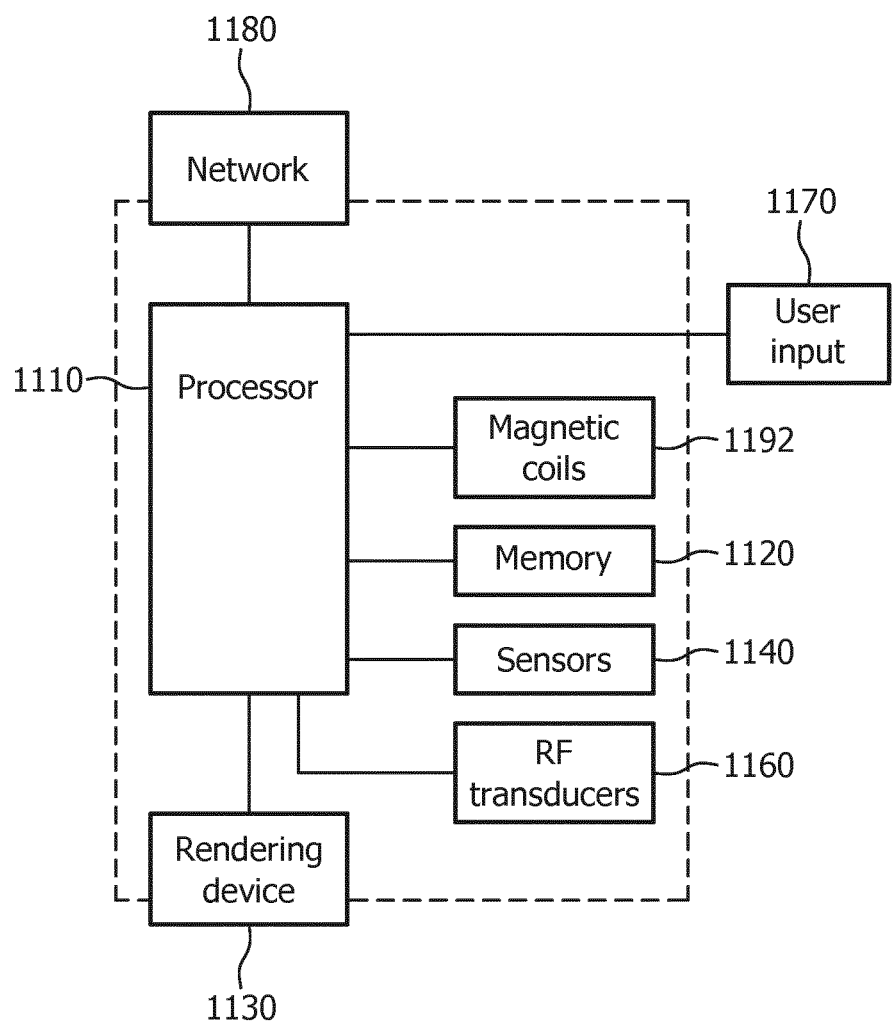
FIG. 11 shows a portion of a system in accordance with embodiments of the present system.

FIG. 11 shows a portion of a system 1100 in accordance with embodiments of the present system. For example, a portion of the present system may include a processor 1110 (e.g., a controller) operationally coupled to a memory 1120, a user interface (UI) including a rendering device such as a display 1130, sensors 1140, an RF portion 1160, magnetic coils 1192, and a user input device 1170. The memory 1120 may be any type of device for storing application data as well as other data related to the described operation. The application data and other data are received by the processor 1110 for configuring (e.g., programming) the processor 1110 to perform operation acts in accordance with the present system. The processor 1110 so configured becomes a special purpose machine particularly suited for performing in accordance with embodiments of the present system.

The operation acts may include configuring an MRI system by, for example, controlling the magnetic coils 1192, and/or the RF portion 1160 in accordance with system settings. An optional location mechanism may control a physical location (e.g., in x, y, and z axes) of a patient and/or the RF portion 1160, as desired. The RF portion 1160 may be controlled by the processor 1110 to control RF transducers such as RF transmission coils and RF reception coils, and RF states (modes) such as tune/detune and synchronization states. The RF portion 1160 may include wired- and/or wireless-type RF portions which may be local and/or remote from each other. In accordance with embodiments, the RF portion 1160 may include a wireless receive-type RF coil such as provided in one or more of a base, positioner and/or top portion. The magnetic coils 1192 may include main magnetic coils, gradient coils ($G_R$) (e.g., x-, y-, and z-gradient coils), optional gradient shimming coils, and may be controlled to emit a main magnetic field ($B_0$) and/or gradient fields in a desired direction and/or strength (e.g., $G_x$, $G_y$, and $G_z$). The processor 1110 may control one or more power supplies to provide power to the magnetic coils 1192 so that a desired magnetic field is emitted at a desired time. The RF portion 1160 may be controlled to transmit RF pulses and to receive induced MR signals (e.g., echo information). A processor or portion thereof operating as a reconstructor may process received signals such as the induced MR signals and transform these signals (e.g., using one or more reconstruction techniques of embodiments of the present system) into content which may include image information (e.g., still or video images (e.g., video information)), data, and/or graphs (e.g., spectrographic information) that may be rendered on, for example, a UI of the system such as on the display 1130, a speaker, etc. Further, the content may then be stored in a memory of the system such as the memory 1120 for later use. Thus, operation acts may include requesting, providing, and/or rendering of content such as, for example, reconstructed image information obtained from the induced MR information. The processor 1110 may render the content such as video information on a UI of the system such as a display of the system.

The user input 1170 may include a keyboard, a mouse, a trackball, or other device, such as a touch-sensitive display, which may be stand alone or part of a system, such as part of a personal computer, a personal digital assistant (PDA), a mobile phone (e.g., a smart phone), a monitor, a smart or dumb terminal or other device for communicating with the processor 1110 via any operable link such as a wired and/or wireless communication link. The user input device 1170 may be operable for interacting with the processor 1110 including enabling interaction within a UI as described herein. Clearly the processor 1110, the memory 1120, display 1130, and/or user input device 1170 may all or partly be a portion of a computer system or other device such as a client and/or server.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 1120 or other memory coupled to the processor 1110.

The program and/or program portions contained in the memory 1120 may configure the processor 1110 to implement the methods, operational acts, and functions disclosed herein. The memories may be distributed, for example between the clients and/or servers, or local, and the processor 1110, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 1110. With this definition, information accessible through a network is still within the memory, for instance, because the processor 1110 may retrieve the information from the network for operation in accordance with the present system.

The processor 1110 is operable for providing control signals and/or performing operations in response to input signals from the user input device 1170 as well as in response to other devices of a network and executing instructions stored in the memory 1120. The processor 1110 may include one or more of a microprocessor, an application-specific or general-use integrated circuit(s), a logic device, etc. Further, the processor 1110 may be a dedicated processor for performing in accordance with the present system or may be a general-purpose processor wherein only one of many functions operates for performing in accordance with the present system. The processor 1110 may operate utilizing a program portion, multiple program segments, or may be a hardware device utilizing a dedicated or multi-purpose integrated circuit. Embodiments of the present system may provide fast imaging methods to acquire and/or reconstruct images. Suitable applications may include imaging systems such as MRI systems.

Accordingly, embodiments of the present system may provide RF coil arrays such as a knee coil array having a body including first, second and third parts such as a base, a positioner and an upper section, respectively, one or more of which may include an RF coil array having coil elements. The positioner may be formed as a thin sheet and may couple to the base so as to assist in positioning the upper section. In accordance with embodiments of the present system, the positioner may be a disposable single-use positioner or may be reusable as desired. As an added advantage, when two or more of the base, the positioner and the upper section include an RF coil array, the coil elements in these RF coil arrays may be substantially isolated from the coil elements in the other RF coil array. The arrangement of the RF coil arrays provides for a wide range of patient sizes while delivering near optimal performance when performing MR acquisition.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

The invention claimed is:

1. A radio-frequency (RF) coil apparatus for magnetic resonance (MR) systems, the RF coil comprising:
   a base having opposed sides, a surface to support an object of interest (OOI) for scanning, and fasteners situated at the opposed sides;
   a positioner configured to be releasably attached to the base and having a body extending between opposed ends and fasteners situated at the opposed ends of the body, the body configured to form an arch between the opposed ends wherein the body is formed around a length of the object of interest and is configured to enhance rigidity of the positioner in a plane perpendicular to the length of the object of interest; and
   an upper section having at least one RF coil array for acquiring induced MR signals, the upper section configured to be positioned over the positioner, wherein the positioner is configured to support the upper section without placing pressure or weight on the object of interest and to guide and support the upper section.

2. The apparatus of claim 1, wherein the fasteners of the positioner are configured to couple to corresponding fasteners of the base.

3. The apparatus of claim 1, wherein the fasteners of the base and the positioner are corresponding hook-and-loop type fasteners.

4. The apparatus of claim 1, wherein at least one of the fasteners of the positioner comprises a tab suitable for grasping by a user.

5. The apparatus of claim 1, wherein the positioner is a U-shaped arch formed from transparent, semi-transparent, or translucent plastic.

6. The apparatus of claim 1, wherein the positioner comprises a unitary U-shaped arch with opposed flanges at opposed ends of the arch.

7. The apparatus of claim 6, wherein the opposed flanges are configured to support the upper section in a fixed position on the positioner.

8. The apparatus of claim 6, wherein a height at which the upper section is supported is adjustable.

9. The apparatus of claim 1, wherein the positioner includes an arch with opposite lower ends, the lower ends being configured to support the arch in a fixed alignment with the base.

10. The apparatus of claim 1, wherein the base further comprises at least one RF coil array for acquiring induced MR signals.

11. The apparatus of claim 10, further comprising a communication link configured to couple the RF coil arrays of the base and the upper section.

12. The apparatus of claim 1, wherein an arch shaped upper surface of the positioner and an under surface the upper section are complementary.

13. A radio-frequency (RF) coil apparatus for magnetic resonance (MR) systems, the RF coil comprising:
 a base having opposed sides and a surface configured to support an object of interest for scanning;
 a positioner in a form of a fixed arch with ends configured to be supported on and aligned with the base to define an arched tubular region for the object of interest;
 fasteners configured to detachably attach the lower ends of the positioner to the base to form the arched tubular region around the object of interest for MR imaging and detach the lower ends of the positioner from the base to facilitate removal of the object of interest; and
 an upper section having at least one RF coil array for acquiring induced MR signals and having a lower surface configured to be positioned over and supported by the positioner and to increase rigidity of the positioner.

14. The apparatus of claim 13, wherein the positioner further comprises opposed flanges extending outward from the lower edges of the positioner and configured to be supported by the base.

15. The apparatus of claim 13, wherein the positioner includes a bendable sheet configured to be bent into a C-shape or U-shape to define the fixed arch.

16. A process of configuring a radio-frequency (RF) coil for scanning an object of interest (OOI), the process comprising acts of:
 positioning the OOI upon a support surface of a base, the base having opposed sides and base fasteners situated on each of the opposed sides;
 lowering a positioner over the OOI, the positioner having an arched body extending between opposed ends and positioner fasteners situated at the opposed ends of the arched body;
 after lowering the positioner over the OOI, coupling the positioner to the base by attaching the positioner fasteners of the positioner to adjacent corresponding base fasteners of the base; and
 guiding, by the positioner, an upper section into a desired position relative to the OOI, the upper section having at least one RF coil array configured for acquiring induced MR signals, the upper section having a lower surface configured to be disposed on and supported by an upper surface of the positioner.

17. The method of claim 16, further comprising an act of coupling a communication link between the base and the upper section.

18. The method of claim 16, wherein the upper section conforms to an outer surface of the arched body and enhances a rigidity of the arched body when supported on the positioner.

19. The method of claim 16, further comprising an act of enhancing rigidity of the positioner using the upper section.

20. The method of claim 16, wherein the positioner includes a flexible sheet carrying the positioner fasteners along opposite edges and lowering the positioner over the OOI includes disposing a central portion of the flexible sheet over the OOI, bending the opposite ends of the flexible sheet to form the arched body, and attaching the positioner fasteners to the base fasteners to hold the sheet in an arched configuration.

* * * * *